(12) United States Patent
Merino et al.

(10) Patent No.: US 11,896,545 B2
(45) Date of Patent: Feb. 13, 2024

(54) VIBRATING GARMENT ASSEMBLY

(71) Applicant: Therabody, Inc., Los Angeles, CA (US)

(72) Inventors: Eduardo Merino, Los Angeles, CA (US); Benjamin Nazarian, Los Angeles, CA (US); Jaime Sanchez Solana, Los Angeles, CA (US)

(73) Assignee: Therabody, Inc., Los Angeles, CA (US)

( * ) Notice: Subject to any disclaimer, the term of this patent is extended or adjusted under 35 U.S.C. 154(b) by 0 days.

(21) Appl. No.: 17/678,924

(22) Filed: Feb. 23, 2022

(65) Prior Publication Data

US 2022/0265507 A1    Aug. 25, 2022

Related U.S. Application Data

(63) Continuation-in-part of application No. 17/406,478, filed on Aug. 19, 2021, now Pat. No. 11,547,627,
(Continued)

(51) Int. Cl.
*A61H 23/02* (2006.01)
*A41D 27/10* (2006.01)

(52) U.S. Cl.
CPC ......... *A61H 23/0254* (2013.01); *A41D 27/10* (2013.01); *A41D 2400/322* (2013.01);
(Continued)

(58) Field of Classification Search
CPC ........ A61H 23/0254; A61H 2023/0272; A61H 2201/165; A61H 2201/5025;
(Continued)

(56) References Cited

U.S. PATENT DOCUMENTS

| 1,545,027 A | 7/1925 | Ashlock |
| D143,678 S | 1/1946 | Snyder et al. |

(Continued)

FOREIGN PATENT DOCUMENTS

| CN | 201239336 Y | 5/2009 |
| CN | 301664182 S | 9/2011 |

(Continued)

OTHER PUBLICATIONS

Mueller Group, "Wire and Cable from the Future," Jan. 3, 2012, accessed from URL: https://muellergroup.wordpress.com/tag/stretchable-wire/ (Year: 2012).*

(Continued)

*Primary Examiner* — Justine R Yu
*Assistant Examiner* — Benjamin M. Kusiak
(74) *Attorney, Agent, or Firm* — Sterne, Kessler, Goldstein & Fox P.L.L.C.

(57) ABSTRACT

A garment assembly includes a sleeve member having outer and inner surfaces, a first vibration assembly associated with the sleeve member, and a control module associated with the sleeve member. The first vibration assembly includes a plurality of vibration motors that are arranged in a circle about a center point. An angular distance between each vibration motor of the plurality of vibration motors is approximately the same. The control module includes a battery, and the first vibration assembly is in electrical communication with the control module.

21 Claims, 15 Drawing Sheets

Related U.S. Application Data which is a continuation-in-part of application No. 17/066,230, filed on Oct. 8, 2020, now Pat. No. 11,432,994, which is a continuation-in-part of application No. 16/796,143, filed on Feb. 20, 2020, now Pat. No. 10,940,081.

(60) Provisional application No. 63/164,829, filed on Mar. 23, 2021, provisional application No. 63/068,123, filed on Aug. 20, 2020, provisional application No. 62/912,392, filed on Oct. 8, 2019, provisional application No. 62/899,098, filed on Sep. 11, 2019, provisional application No. 62/844,424, filed on May 7, 2019.

(52) U.S. Cl.
CPC ............... *A61H 2023/0272* (2013.01); *A61H 2201/165* (2013.01); *A61H 2201/5025* (2013.01); *A61H 2201/5064* (2013.01)

(58) Field of Classification Search
CPC .......... A61H 2201/5064; A61H 23/006; A61H 23/008; A61H 23/02; A61H 2205/06; A61H 2205/10; A61H 2201/0157; A61H 2201/0107; A61H 2201/12; A61H 2201/1207; A61H 2201/1215; A61H 2201/1609–1616; A61H 2201/1652; A61H 2201/1654; A61H 2201/1695; A61H 23/00004; A61H 23/0218; A61H 23/0236; A61H 23/0245; A61H 23/0263; A61H 2023/002; A61H 2023/0209; A61H 2023/0227; A61H 2023/0281; A61H 2023/029; A61H 2230/04–065; A61H 2230/085; A61H 2230/208; A61H 2230/50; A61H 2201/0111; A61H 2201/0153; A61H 2201/1635–1647; A61H 2201/5007–5012; A61H 2201/5028; A61H 2201/5035; A61H 2201/5082; A61H 2201/5089; A61H 2201/5097; A41D 27/10; A41D 2400/322; A41D 13/08; A41D 1/002; A41D 27/205; A41D 7/0044; A41D 7/0045; H02J 7/0042; H02J 7/0044; H02J 7/0045; Y10T 24/32; F16B 2001/0035
USPC .......... 601/46; 2/59, 125, 126, 16, 247–251; 320/107, 113; 439/37
See application file for complete search history.

(56) References Cited

U.S. PATENT DOCUMENTS

| | | | |
|---|---|---|---|
| 2,987,334 A | 6/1961 | Wendling | |
| 3,557,781 A * | 1/1971 | Kaye, Sr. | A61H 23/0263 601/71 |
| 3,705,579 A | 12/1972 | Morini et al. | |
| D230,522 S | 2/1974 | Rothman | |
| 4,046,142 A | 9/1977 | Whitney | |
| 4,257,408 A * | 3/1981 | Ramey | A63H 3/001 601/46 |
| 4,935,972 A * | 6/1990 | Brady | H05K 7/06 5/915 |
| 4,979,502 A * | 12/1990 | Hunt | A61H 23/02 601/79 |
| 5,103,809 A | 4/1992 | DeLuca et al. | |
| 5,334,131 A * | 8/1994 | Omandam | A61H 23/0263 601/70 |
| 5,545,125 A * | 8/1996 | Tseng | A61H 23/0263 601/70 |
| 5,605,144 A * | 2/1997 | Simmons | A42B 3/10 2/171.2 |
| 5,902,256 A * | 5/1999 | Benaron | A61H 23/0263 601/60 |
| 6,093,164 A * | 7/2000 | Davis | A61H 23/0263 602/61 |
| D439,984 S | 4/2001 | Thach | |
| 6,537,235 B1 * | 3/2003 | Connor | A61H 23/0263 601/70 |
| 6,823,762 B2 | 11/2004 | Hu | |
| 6,833,639 B2 | 12/2004 | Lau et al. | |
| 6,895,261 B1 * | 5/2005 | Palamides | H04B 1/385 455/100 |
| 7,085,585 B2 | 8/2006 | Camarillo et al. | |
| 7,147,610 B2 | 12/2006 | Maalouf | |
| 7,242,118 B2 | 7/2007 | Sakamoto | |
| 7,279,814 B2 | 10/2007 | Patt et al. | |
| 7,431,706 B2 | 10/2008 | Louis | |
| 7,474,018 B2 | 1/2009 | Shimizu et al. | |
| 7,732,951 B2 | 6/2010 | Mukaide | |
| 7,898,121 B2 | 3/2011 | Ramsay et al. | |
| 7,927,259 B1 | 4/2011 | Rix | |
| 7,927,294 B2 | 4/2011 | Kamimura et al. | |
| 8,120,225 B2 | 2/2012 | Thundat et al. | |
| D659,644 S | 5/2012 | Gretz | |
| 8,324,763 B2 | 12/2012 | Gosvener | |
| 8,344,560 B2 | 1/2013 | Gosvener | |
| 8,415,839 B2 | 4/2013 | Geng et al. | |
| 8,523,793 B1 * | 9/2013 | Waldon, Sr. | A61H 23/02 601/87 |
| 8,587,163 B2 | 11/2013 | Camacho | |
| 8,624,448 B2 | 1/2014 | Kaiser et al. | |
| 8,777,881 B2 | 7/2014 | Tsai | |
| 8,786,143 B2 | 7/2014 | Gosvener | |
| 9,161,878 B1 | 10/2015 | Pamplin et al. | |
| 9,236,786 B1 | 1/2016 | Geng et al. | |
| D756,180 S | 5/2016 | Chen | |
| 9,411,060 B2 | 8/2016 | Coste | |
| 9,412,507 B2 | 8/2016 | Blanding et al. | |
| 9,889,066 B2 | 2/2018 | Danby et al. | |
| D817,732 S | 5/2018 | Rettler | |
| 10,159,623 B2 | 12/2018 | Leftly | |
| D837,395 S | 1/2019 | Gan | |
| 10,601,293 B2 | 3/2020 | Hutchins et al. | |
| 10,610,446 B2 | 4/2020 | Shockley, Jr. et al. | |
| 10,774,696 B2 | 9/2020 | Hutchins | |
| 10,855,155 B2 | 12/2020 | Huang et al. | |
| 10,938,286 B1 | 3/2021 | Liu et al. | |
| 2004/0009731 A1 * | 1/2004 | Rabinowicz | A61N 1/04 2/456 |
| 2005/0209545 A1 | 9/2005 | Farrow | |
| 2006/0064800 A1 * | 3/2006 | Freund | A61F 13/085 2/446 |
| 2006/0238055 A1 | 10/2006 | Danford | |
| 2007/0179421 A1 | 8/2007 | Farrow | |
| 2007/0245444 A1 * | 10/2007 | Brink | A41D 1/04 2/69 |
| 2008/0001484 A1 | 1/2008 | Fuller et al. | |
| 2008/0201818 A1 * | 8/2008 | Nilforushan | A61F 7/02 607/114 |
| 2009/0112134 A1 | 4/2009 | Avni | |
| 2009/0143706 A1 | 6/2009 | Acosta | |
| 2009/0143707 A1 | 6/2009 | Strahl | |
| 2009/0234262 A1 * | 9/2009 | Reid, Jr. | A61B 5/0022 600/595 |
| 2010/0249637 A1 * | 9/2010 | Walter | A61H 23/02 601/46 |
| 2011/0257575 A1 | 10/2011 | Farrow | |
| 2011/0277204 A1 | 11/2011 | Chan | |
| 2012/0059294 A1 | 3/2012 | Schubert | |
| 2012/0119594 A1 | 5/2012 | Gosvener | |
| 2012/0185999 A1 * | 7/2012 | Raviv | A41D 27/205 2/247 |
| 2012/0222333 A1 * | 9/2012 | Short | A61H 23/00 12/146 M |
| 2012/0259255 A1 * | 10/2012 | Tomlinson | A61H 23/0218 601/46 |
| 2013/0116606 A1 | 5/2013 | Cordo | |

(56) References Cited

U.S. PATENT DOCUMENTS

| | | | |
|---|---|---|---|
| 2014/0111034 A1 | 4/2014 | Gosvener | |
| 2014/0111035 A1 | 4/2014 | Gosvener | |
| 2014/0117786 A1 | 5/2014 | Gosvener | |
| 2014/0144624 A1 | 5/2014 | Camacho Cardenas | |
| 2014/0305441 A1 | 10/2014 | Porter | |
| 2014/0317825 A1* | 10/2014 | Silverberg | A41D 13/1209 2/69 |
| 2014/0364778 A1 | 12/2014 | Leftly | |
| 2015/0214760 A1* | 7/2015 | Chraime | H02J 7/0045 320/103 |
| 2015/0272815 A1* | 10/2015 | Kitchens | A61H 23/0263 601/46 |
| 2015/0290028 A1 | 10/2015 | Isserow | |
| 2016/0008217 A1 | 1/2016 | Constantine | |
| 2016/0022536 A1 | 1/2016 | Nauman | |
| 2016/0184171 A1 | 6/2016 | Poole | |
| 2016/0331620 A1* | 11/2016 | Kazanchyan | A61N 1/36003 |
| 2016/0367425 A1 | 12/2016 | Wersland | |
| 2017/0042754 A1 | 2/2017 | Fowers et al. | |
| 2017/0119620 A1* | 5/2017 | Trapp | A61H 11/00 |
| 2017/0304145 A1 | 10/2017 | Pepe | |
| 2017/0332706 A1* | 11/2017 | Gellineau | A41D 1/002 |
| 2018/0038363 A1 | 2/2018 | Trethewey | |
| 2018/0141188 A1 | 5/2018 | Lai | |
| 2018/0199635 A1 | 7/2018 | Longinotti-Buitoni | |
| 2018/0271209 A1* | 9/2018 | Zahrieh | A61H 39/007 |
| 2018/0303704 A1 | 10/2018 | Idris | |
| 2019/0015295 A1 | 1/2019 | Marton | |
| 2019/0060159 A1* | 2/2019 | Seo | A61H 23/0263 |
| 2019/0183724 A1 | 6/2019 | Sifferlin | |
| 2019/0269880 A1 | 9/2019 | Root | |
| 2019/0283247 A1* | 9/2019 | Chang | A61B 5/7267 |
| 2019/0297970 A1* | 10/2019 | Gramlin | B32B 3/08 |
| 2020/0000677 A1* | 1/2020 | Pamplin | A61H 7/001 |
| 2020/0022864 A1 | 1/2020 | Lee | |
| 2020/0085116 A1* | 3/2020 | Harris | A61H 23/0245 |
| 2020/0100981 A1 | 4/2020 | Bobey et al. | |
| 2020/0121550 A1* | 4/2020 | Elliot | A61H 11/00 |
| 2020/0214927 A1* | 7/2020 | Clowney | A61H 39/04 |
| 2020/0281813 A1* | 9/2020 | Chao | A61H 39/002 |
| 2021/0022955 A1 | 1/2021 | Wersland et al. | |
| 2021/0093023 A1* | 4/2021 | Kuhner-Stout | A41D 13/02 |
| 2021/0098651 A1* | 4/2021 | Luo | H01L 33/343 |
| 2021/0111591 A1* | 4/2021 | Chaudhri | H02J 7/02 |
| 2021/0330539 A1 | 10/2021 | Faussett | |

FOREIGN PATENT DOCUMENTS

| | | |
|---|---|---|
| CN | 202637439 U | 1/2013 |
| CN | 303250924 S | 6/2015 |
| CN | 303250929 S | 6/2015 |
| CN | 106859949 A | 6/2017 |
| CN | 304561844 S | 3/2018 |
| CN | 207855923 U | 9/2018 |
| CN | 109528473 A | 3/2019 |
| JP | S5428491 A | 3/1979 |
| JP | H0447440 U | 4/1992 |
| JP | 2000189525 A | 7/2000 |
| JP | 2011502369 A | 1/2011 |
| JP | 5129032 B2 | 1/2013 |
| JP | 2014511240 A | 5/2014 |
| KR | 101162978 B1 | 7/2012 |
| KR | 20170108550 A | 9/2017 |
| TW | I359657 B | 3/2012 |
| WO | WO-0100269 A1 | 1/2001 |

OTHER PUBLICATIONS

U.S. Appl. No. 62/554,554, filed Mar. 7, 2001, Turtzo.
International Search Report and Written Opinion issued in PCT/US21/46651.
BriskHeat Corporation, BriskHeat HSTAT.
Anthony Katz, "The RAPTOR: Helps Patients and Saves Your Most Valuable Tool .. . Your Hands," DC Aligned:MeyerDC, Dec. 9, 2015, available at: http://news.meyerdc.com/community/vendor-spotlight/the-raptor-helps-patients-saves-your-most-valuable-tool-your-hands/ (last visited Feb. 15, 2023); 5 pages.
Ball P., "Stretchy Wires Form Bendy Circuits," Nature, Mar. 15, 2004, vol. 93, No. 1, 3 Pages.
Defendant's Initial Invalidity Contentions, *Therabody, Inc.* v. *Tzumi Electronics LLC et al.*, Case No. SDNY-1-21-cv-07803 (PGG)(RWL), dated Aug. 17, 2022; 16 pages.
Description of Therabody GI Device, available at: https://www.therabody.com/US/en-us/faq/thearagun-devices/faq-devices-1.html?fdid=faq&csortb1=sortOrder&csortd1=1 (last visited Feb. 15, 2023).
Holly Riddle, "Theragun vs. Hyperice vs, Hydragun: Massage Gun Showdown [Buyer's Guide]," ChatterSource: Health & Wellness, Mar. 9, 2021, available at: https://www.chattersource.com/article/massage-gun/ (last visited Feb. 17, 2023); 14 pages.
International Preliminary Report on Patentability for International Application No. PCT/US2021/046651, dated Mar. 2, 2023, 10 Pages.
Visual Description of Hyper Ice, Inc. Raptor Device, "Osteopatia Haidy Ortale—Raptor Massage," available at: https://www.youtube.com/watch?v=plyW8FBowVs (last visited Feb. 15, 2023); 1 page.
Visual Description of Hyper Ice, Inc. Raptor Device, "RAPTOR Solutions 1.3 Prone," available at: https://www.youtube.com/watch?v=6i1tRqdwPU8&t=156s (last visited Feb. 15, 2023); 1 page.
Written Opinion for International Application No. PCT/US2023/063004 dated Jul. 28, 2023, 14 pages.

* cited by examiner

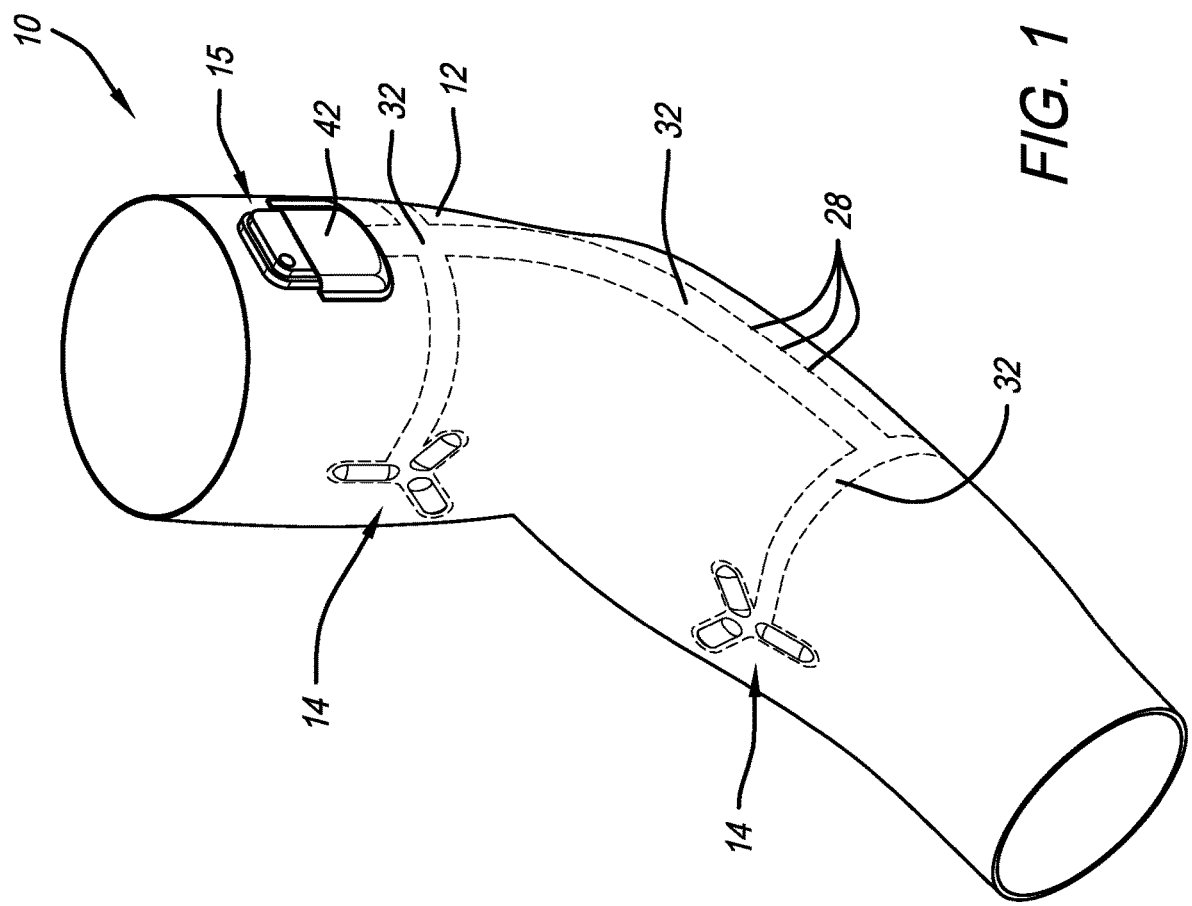

VIBRATING GARMENT ASSEMBLY

CROSS-REFERENCE TO RELATED APPLICATIONS

This application is a continuation-in-part of U.S. application Ser. No. 17/406,478, filed on Aug. 19, 2021, which claims the benefit of U.S. Provisional Application No. 63/164,829, filed on Mar. 23, 2021 and U.S. Provisional Application No. 63/068,123, filed on Aug. 20, 2020. This application is also a continuation-in-part of U.S. application Ser. No. 17/066,230, filed on Oct. 8, 2020, which is a continuation-in-part of U.S. patent application Ser. No. 16/796,143, filed Feb. 20, 2020, now U.S. Pat. No. 10,940,081, which claims the benefit of U.S. Provisional Application No. 62/912,392, filed Oct. 8, 2019, U.S. Provisional Application No. 62/899,098, filed Sep. 11, 2019 and U.S. Provisional Application No. 62/844,424, filed May 7, 2019, all of which are incorporated by reference herein in their entireties.

FIELD OF THE INVENTION

The present invention relates to a vibrating garment assembly, and more particularly to a vibrating garment assembly that includes sets of vibrating devices.

BACKGROUND OF THE INVENTION

Massage and therapeutic devices for recovery after working out and the like are known. However, garments, straps or sleeves that include vibration therapy directed to specific body parts or muscles are needed.

The background description disclosed anywhere in this patent application includes information that may be useful in understanding the present invention. It is not an admission that any of the information provided herein is prior art or relevant to the presently claimed invention, or that any publication specifically or implicitly referenced is prior art.

SUMMARY OF THE PREFERRED EMBODIMENTS

In accordance with another aspect of the present invention, there is provided a garment assembly that includes a first sleeve member, a first vibration assembly associated with the first sleeve member, and a control module. The first vibration assembly includes a plurality of vibration devices that are arranged in a circle about a center point. The angular distance between each vibration device in the plurality of vibration devices is approximately the same. The control module is associated with the first sleeve member, and includes a battery. The first vibration assembly is in electrical communication with the control module. It will be appreciated that electrical communication can include both power and data communication. In a preferred embodiment, the first vibration assembly includes first, second and third vibration devices. The angular distance between the first vibration device and the second vibration device is approximately 120°, the angular distance between the first vibration device and the third vibration device is approximately 120°, and the angular distance between the third vibration device and the second vibration device is approximately 120°. Preferably, the first, second and third vibration devices define first, second and third axes, respectively, the first, second and third axes are co-planar and the second axis is approximately 120° from the first axis, the third axis is approximately 120° from the first axis, and the third axis is approximately 120° from the second axis.

In a preferred embodiment, the garment assembly includes a second sleeve member disposed within the first sleeve member and the first vibration assembly is sandwiched between the first and second sleeve members. Preferably, the garment assembly includes a first vibration assembly pocket that contains the first vibration assembly and that is defined by stitches that connect the first sleeve member to the second sleeve member and at least partially surround the plurality of vibration devices in the first vibration assembly.

In a preferred embodiment, the garment assembly incudes one or more electrical communication strips that electrically communicates the control module and the vibration assemblies. The electrical communication strip includes at least a first wire that is not straight (so as to provide slack to allow the wire to move when the garment stretches) and that is associated with an elastic band.

In a preferred embodiment, the garment assembly includes one or more tunnel that contain the electrical communication strip(s) and that are defined by stitches that connect the first sleeve member to the second sleeve member and at least partially surround the electrical communication strip. The electrical communication strip(s) extend through the tunnels between the control module and the one or more vibration assemblies.

Preferably, the garment assembly includes a control module pocket that receives at least a portion of the control module (or where the control module is positioned). The battery can be removed from the control module through the control module pocket.

In a preferred embodiment, the first sleeve member includes a distal end and a proximal end and a sleeve length is defined between the proximal end and the distal end. The first sleeve member and/or the second sleeve member (which may be referred to as a sleeve assembly) include(s) a first section with a first compression value and a second section with a second compression value. The second section is defined between the first section and the proximal end and the first compression value is greater than the second compression value. In a preferred embodiment, the first sleeve defines a sleeve length between a distal end and a proximal end, and the first sleeve member comprises a material that includes a range of compression values that decrease between the distal end and the proximal end. The compression values can decrease gradually. The range can include between 2-30 sections or values and preferably between 2-10 sections or values.

Described herein is a garment assembly that includes vibration therapy integrated therein. The garment assembly may be embodied in a sleeve. However, it will be appreciated that this is not a limitation on the present invention and the garment assembly can be any type of wearable garment.

In a preferred embodiment, the garment assembly includes an inner fabric layer or sleeve, an outer fabric layer or sleeve and a vibration layer that includes a plurality of vibration devices. The inner and outer fabric layers sandwich the vibration layer and the vibration devices therebetween. The vibration devices and related components can be housed in a housing (flexible or hard) or secured on a bracket, PCB, or layer.

In a preferred embodiment, the garment assembly also includes sensors. The sensors can be part of the vibration layer, the sensors can be a separate layer or at least some of the sensors can be embedded in or positioned on the inner surface of the inner fabric layer so that the sensor or sensors are positioned adjacent to or in contact with the wearer's skin (e.g., to sense the wearer's heart rate). Any type of sensor or any of the sensors discussed herein can be included. The vibration layer can include a fill material in which the vibration devices are embedded. The vibration layer (or any of the other layers) also include cabling or wiring 2 (and defined pathways therefor) for electrical or data connection or communication between the various components, as necessary.

The vibration devices can be secured to the surface of the inner and/or outer layer. A vibration suppression layer can be included on the outside (e.g., between the vibration devices and the outer layer or outside of the outer layer) to prevent the outer layer or outside of the garment assembly from vibrating or to lessen the vibrations on the outside. A vibration amplifying layer can be included on the inside (e.g., between the vibration devices and the inner layer or inside of the inner layer) to transmit and distribute or spread out the vibrations from the plurality of vibration devices to further be transmitted to the wearer.

In a preferred embodiment, the garment assembly includes wireless communication or connectivity (e.g., BLUETOOTH®) so that it can communicate with a software application on a mobile device, such as a phone to provide a "smart" garment system. For example, see a similar smart system or intelligence method disclosed in U.S. Publication No. 2021/0022955 (the "'955 publication"), the entirety of which is incorporated by reference herein. The wireless communication device can be housed on a PCB that may or may not be a part of a control module and that is also in electrical and/or data communication with the vibration devices and various sensors.

The vibration device may include a rotating weight that provides the vibration, a rotating shaft for rotating the weight and coils that generate a magnetic field to rotate the shaft. It will be appreciated that this type of motor is not a limitation on the present invention. Any type of motor that provides the desired vibration or amplitude is within the scope of the present invention. For example, the motor can include an electromagnet coil through which a shaft extends and where the shaft reciprocates (is pushed and pulled) as a result of the magnetic field produced by the coil. The shaft can include some type of member or portion thereon that provides the vibration or percussion on the wearer's skin.

The garment assembly may include vibration modules, assemblies or devices that are disposed anywhere throughout the garment assembly and can be positioned to cover or affect different body parts or muscles. In an embodiment, the vibration modules can be removable. The garment assembly may include a plurality of locations where a vibration module can be secured or attached thereto. This gives the user wearing the garment (e.g., sleeve or shirt) a plurality of options for where to position one or more modules. For example, if the user has a right shoulder issue they are treating, they may only place one or more modules in that location. At a later time they can use the same shirt to treat an abdominal issue.

In a preferred embodiment, the garment assembly is embodied in a knee wrap or sleeve that includes vibration assemblies. The vibration devices may be are embedded in the garment portion (e.g., between inner and outer fabric layers). It will be appreciated that any configuration of vibration devices is within the scope of the present invention. The vibration devices can be configured to treat certain issues and can be placed in patterns around the sleeve or wrap, such as a triangle, star, circle, spiral, other pattern, etc. and can increase blood flow and provide therapeutic benefit as desired.

The garment assembly may include a plurality of magnets that may be overlapping or a single magnet with a plurality of locations where the magnet on the module can be placed in order to allow the modules to be movable or positionable within the same general area. This allows the user to move the module to the exact location of the issue. It also allows a single garment size to be usable by different uses (because no two bodies are exactly the same). In another embodiment, the majority of or all of the garment can be magnetized, thus allowing the module to attach anywhere.

In a preferred embodiment, the invention includes a smart vibration system. It will be appreciated by those of ordinary skill in the art that at a certain frequency (depending on the mass attached to the system), vibrations can make a user's body resonate and therefore increase the amplitude of the perceived vibration. To take advantage of this resonant frequency principle (which is different from person to person and from body part to body part), the present invention may include a closed loop system with sensors that scan through the different speeds of the vibration devices or motors until the resonant frequency is found. One way to achieve this is by adding accelerometers near the motor locations that can measure the actual vibration it is being generated when the motor is attached to the body part. In an exemplary embodiment, strain gages that can measure displacement of the garment are included in the location of the motor.

In a preferred embodiment, the garment assembly is washable and includes at least some components that are embedded in, attached to, etc. permanently in the garment (e.g., waterproof enclosed motors, cabling, etc) and other components that are removable (battery pack, control module, PCB). The permanent components are preferably sealed in the garment (e.g., between garment layers and the user can wash the garment after removing the power unit system or at least a portion thereof (battery pack, control module, PCB, etc.).

One or more of the layers of the device can include vibration capability. The modules or assemblies may be different sizes depending on the muscle group or the surface area desired be treated. The device (or separate devices) may also include different sized and shaped straps to accommodate different body parts.

In a preferred embodiment, the garment assembly includes a control member and/or battery pack secured to or associated with the garment. In this embodiment the battery pack may also be removable (e.g., it is clipped onto the garment or placed in a pocket). The controller can be electrically connected to and in data communication with the modules so that the modules are powered and can be controlled by the controller. Wiring can be included connecting the battery pack/controller to the modules. The wiring can be embedded in the main body portion and plugs or jacks can be used for attaching and detaching the electrical connections. The wiring can also be external. Wireless connectivity between any and/or all components can also be included.

In another embodiment, a battery can be located in the module, thus making each module independent and interchangeable such that it can be simply placed in the cavity or a strap garment assembly or secured via a magnet or other attachment mechanism to a "wearable" garment assembly. It will be appreciated that the main body portion is made of a material that is pliable and flexible enough to allow the modules to be inserted into the cavities and removed therefrom (e.g., pressed into place and removed therefrom). Vibration devices can also be included embedded in the main body portion or strap portions. It will be appreciated that any and all of the embodiments discussed or disclosed herein and any of the components or concepts included in the embodiments are all completely interchangeable, swappable and usable together. It will be appreciated that strap assemblies, wraps or sleeves can be configured to fit any body part or multiple body parts, e.g., shoulder, back, knee, elbow, wrist, neck, ankle, etc.

The control module or assembly may include a plurality of buttons or switches thereon for controlling the vibration modules. For example, the control module may include a button that turns the device on and off, button(s) for controlling the time or duration, button(s) for changing modes, and button(s) for controlling the vibration devices and turning them on and/or off for various body parts and LED lights related thereto (such as charging indicator(s) and time light indicator(s)). Some of the features are controlled by multiple pushes of the associated button. In an exemplary embodiment, the buttons may work as follows. Pushing the mode button may cycle through the following vibration patterns—constant, wave, regular, wave, off. The time button—one press sets to thirty minutes, two presses sets to sixty minutes, third press for unlimited time. Different vibration assemblies can be activated at different times or for different periods.

One of the advantages of the present invention is the ability to provide flexibility so that the modules can be used on, for example, strap devices and garment or wearable devices. Mounting the modules on strap devices provides high performance and efficacy. The strap allows for multiple modules to work together and treat a wide area. Mounting the modules on a wearable device (e.g., shirt, pants, shorts, etc.) provides the user with the a In preferred embodiments, the garment assemblies can be embodied in arm, leg and calf compression garment assemblies that includes a plurality of vibration assemblies or modules, a battery pack and control module. The battery pack and control module can be located within the same module or assembly. Preferably, at least one of the inner and outer fabric layer(s) are made of a compressive or spandex material so that the garment assembly is form fitting on the wearer's body part. In a preferred embodiment, the vibration modules are received in pockets formed in the garment portion (e.g., between the inner and outer garment layers). The vibration modules can be permanently sewn in the pockets or may be removable. In a preferred embodiment, the battery pack is removable. In another embodiment, the battery pack can be permanent and rechargeable within the garment assembly.

The garment assembly can include BLUETOOTH® BLE wireless connectivity and connections for connecting the battery to the garment assembly, wiring connections, and conductive pathways through and between the inner or outer fabric layer(s) or textile arm sleeve. In an embodiment, the control module is removable together with the battery module as a unit. The control module can include user interface with a plurality of buttons that allow the user to perform functions such as turning the device on and off, activating different vibration modules, starting different routines or preset functions (e.g., pulse, cycle through vibration modules), etc.

The garment assembly may include an outer fabric layer, module or assembly layer, outer film layer (part of the vibration module and covering the vibration motors), electronics layer (the control module), and inner film layer (part of the vibration module and secured on the inner fabric layer). In a preferred embodiment, the vibration motors are arranged in a triangle pattern. In tests, the inventors have determined that this triangular shape intensifies the vibration on the skin or at least increases the vibration intensity perception in the user. In other words, the vibration on the user's skin provided by the three vibration motors arranged in a triangular configuration is greater than the vibration provided by a single vibration motor. In a preferred embodiment, three vibration motors are arranged about 120° apart from one another. In other words, the axis of each vibrating motor is 120° from the axis of the adjacent vibrating motor. Through testing different patterns, the inventors have identified this triangular shape arrangement. In a preferred embodiment, the vibration motors or devices are placed directly in between layers of fabric and secured by adding one or more stitches around each motor.

Any type of manufacturing process is within the scope of the present invention. For example, a cut and sew method can be used where the various layers are cut from layers, pieces or panels of fabric and then sewn together. A knitting method can also be used. With knitting, the thickness, compression level, stretchability and other properties can be varied throughout the garment and/or the individual layers. This method can be performed without the need for any or many seams and is similar to 3D printing. In a preferred embodiment, the garment assembly includes two layers of knitted material with different zones and then the motors and electrical wires and/or cables are sandwiched therebetween and a single seam is used to close the sleeve lengthwise (e.g., along the arm or leg) to create the sleeve interior through which a body part is placed. In another preferred embodiment, the garment assembly includes a single sleeve member that is knitted such that the tunnels for the electrical communication strips or wires and the vibration assembly pockets are created via the knitting process. Preferably, the inner surface of the sleeve includes one or more openings therein so that the electrical communication strips and vibration devices can be inserted therethrough and into the tunnels and vibration assembly pockets. For example, the openings can be located adjacent in the vibration assembly pockets In a preferred embodiment, the wires are part of a flexible or stretchable electronics (or electrical communication) layer, strip or the like. The wires are embedded or stitched into a stretchable fabric member in a pattern (e.g., a wave or zig zag pattern) that provides slack in the wires so that when the stretchable fabric member stretches during use, the wires can move and do not tighten. The electrical communication strip extends between the various vibration modules or assemblies and the battery and/or control module. In a preferred embodiment, the garment assembly includes a docking station or area where the removable and rechargeable battery can be docked to provide power as necessary. The docking station is part of or includes the control module and most, if not all, of the components for controlling the operation of the garment assembly. Preferably, the docking station includes one or more magnets therein that mate or are attracted to one or more magnets in the battery to aid with proper connection and alignment of the battery.

In a preferred embodiment, the garment assembly includes wireless communication so that it can communicate with a software application on a mobile device, such as a phone to provide a "smart" garment system. The wireless communication device can be included on a PCB in the control module that is also in electrical and/or data communication with the vibration devices and various sensors.

The garment assembly can include any of the other features or components discussed herein, and the garment assembly can also include blood flow sensors that provides biometric information to the user regarding whether the device should be used.

In a preferred embodiment, the garment or sleeve includes graded or graduated compression that includes compression that differs over a given distance or over the length of the garment or sleeve. In these garments compression at the distal end (furthest from the heart) is preferably greater than that found at the proximal end (closest to the heart). This compression gradient helps provide improvement in circulation of blood back to the heart. For example, the inventors have learned that in the lower body (e.g., the legs) the minimum compression required to improve venous return is 17.3 mmHg at the calf, decreasing to 15.1 mmHg at the quadriceps. The compression gradient may be gradual between the distal end and the proximal end or the garment may include two or more sections that each have different compression values. For example, an arm sleeve may include a compression of 20 mmHg at the wrist and 15 mmHg at the shoulder. The compression gradient can change gradually (e.g., in increments of 1 mmHg) over the length of the sleeve or the sleeve can include a first section below the elbow (between the wrist and elbow) where the compression is approximately 20 mmHg and a second section above the elbow (between the elbow and the upper arm or shoulder) where the compression is approximately 15 mmHg. The compression value within any portion of the sleeve or garment assembly can be between, for example, approximately 15-20 mmHg for the arm, approximately 10-15 mmHg for the upper leg and approximately 20-30 mmHg for the calf. Approximately means that the value can be within 2 mmHg at either end of a range.

Preferably, the garment assembly also provides localized vibration at the area of the vibration assembly. Local vibration provides rapid oscillatory movement of the tissue and can help increase local blood flow and tissue oxygenation. Pre-exercise local vibration may also be protective, reducing swelling, attenuating the biochemical response to muscle damage, and decreasing pain associated with delayed onset muscle soreness (DOMS). Furthermore, through the stimulus of sensory afferents and mechanoreceptors vibration has been observed to decrease muscle tone, potentiate the stretch reflex, decrease acute muscle pain, and in deconditioned muscles vibration alone may be enough to increase strength. The present invention combines the benefits of compression and vibration into one garment to help the wearer perform and recover. Local vibration has been shown to have both prophylactic and reactive benefits related to circulation, recovery, and pain. Furthermore, it has been associated with being able to help different medical conditions related to both circulatory and neurological disease states. The vibration devices can include vibration frequencies of between 0-300 Hz and vibration amplitudes of between 0.5-12 mm.

In a preferred embodiment, the garment assembly includes one or more biometric sensors or a biometric detection, sensor or tracking system that monitors, determines and analyzes different biometric data or indices of the user. For example, the garment assembly can include the ability to monitor, heart rate/pulse, heart rate variability, blood oxygen letter, skin, muscle or body part temperature. The biometric tracking system may be embodied in a removable assembly, module, housing or the like (similar to the removable battery) and that is in electrical communication with or a part of the control module or assembly. The data and information collected by the biometric tracking system can be communicated to the software application to provide the user with recommendations for use of the garment assembly. The biometric data can also be used to control the vibration assemblies and turn them on and off at different times based on predetermined data points or levels detected by the software (e.g., in the control module or the remote/mobile application). For example, once a predetermined score or level of strain (calculated or otherwise) has been reached or sensed, one or more of the vibration assemblies or individual vibration devices can be switched on (e.g., for a predetermined period of time, in cycles or as otherwise desired or determined by the software).

In a preferred embodiment, the garment assembly includes wireless connectivity ability (e.g., associated with the control module) so that a pair of sleeves or garment assemblies (one for each arm or leg) can be wirelessly paired and communicated to one another with one of the pair connected or communicated to the app/mobile device. In use, the app can then control one sleeve, which then communicates to the other sleeve. This allows synchronization of the motors to operate based on one wireless connectivity slot, or the option to have single use of the sleeve and control the motors via wireless connectivity. In use, the controller can activate individual motors or sets of motors.

Preferably, the sleeve is knitted using a material that comprises polyester with a germanium alloy that naturally emits far infrared (IR) and can provide health benefits. In an exemplary embodiment, the material of the garment, sleeve or sleeve members is 30% nylon and spandex and 70% yarn of polyester infused with germanium alloy. In a preferred embodiment, for the arm related garment assembly, the distance between motor sets are symmetrical circumferentially so that one set ends is associated with or on the bicep and another is associated with or on the triceps no matter the size of the wearer's arm, because the fabric between the sets of motors stretches. The garment can be embodied in sock(s), arm sleeve(s), calf sleeve(s), full leg sleeve(s), pants, shorts, running shorts (with a stretchable under layer that includes the vibration motors and normal/loose shorts over the under layer, as well as other garments.

In a preferred embodiment, the battery pocket includes a front opening for inserting and removing the battery. Preferably, the docking station is attached to the inner surface of the sleeve member and a patch is placed over the back/inner surface of the docking station to provide a comfortable layer against the user's skin. The compression of the sleeve holds the docking station against the user's body part so that it is not loose during a workout or other use. In a preferred embodiment, after removal of the battery, the entire garment assembly is waterproof or water resistant so that it can be washed.

BRIEF DESCRIPTION OF THE DRAWINGS

The invention may be more readily understood by referring to the accompanying drawings in which:

FIG. 1 is a perspective view of a vibrating garment assembly in accordance with a preferred embodiment of the present invention;

Like numerals refer to like parts throughout the several views of the drawings.

DETAILED DESCRIPTION OF THE PREFERRED EMBODIMENTS

Figure 3:
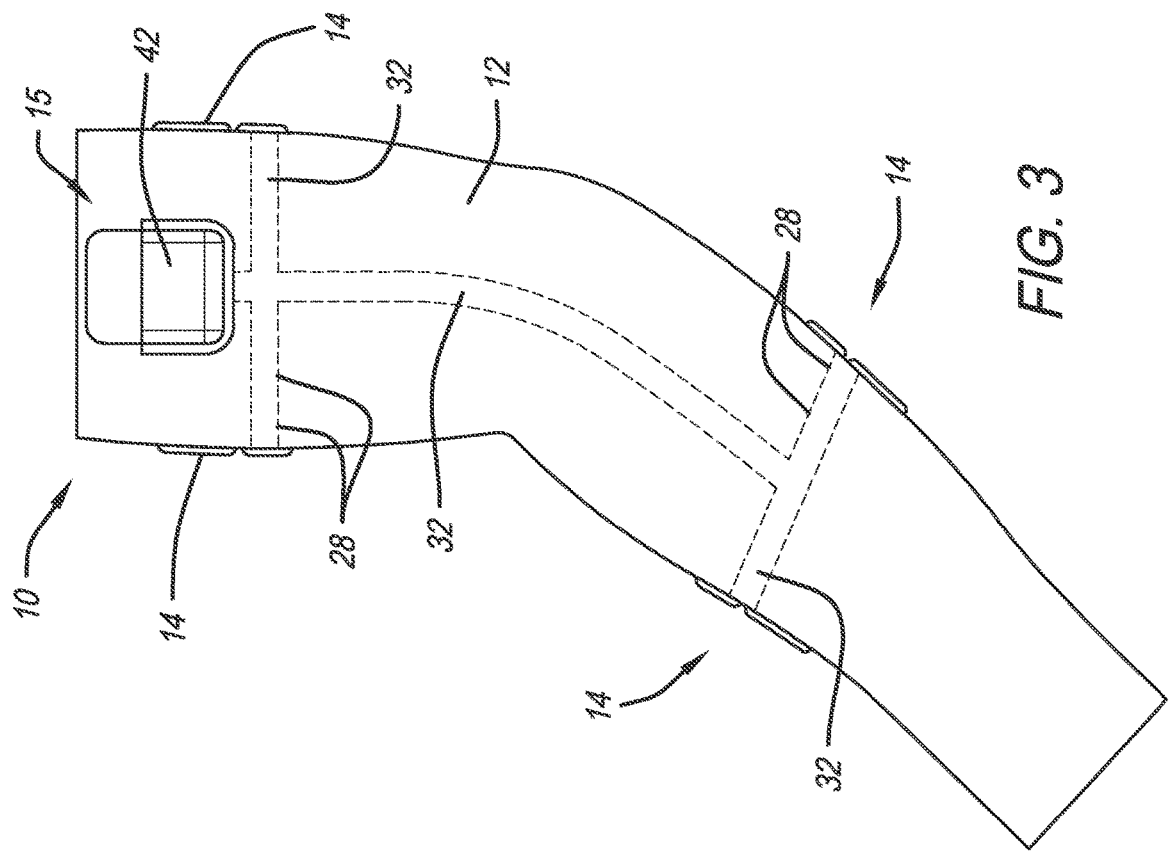
FIG. 3 is a side elevational view of the vibrating garment assembly of FIG. 1.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the-disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

Referring now to the drawings, which are for purposes of illustrating the present invention and not for purposes of limiting the same, the drawings show a vibrating garment or sleeve that provides compression and/or vibration therapy to a wearer. It should be appreciated that the garment can take any wearable form, e.g., a sleeve, shirt, shorts, pants, bodysuit, etc. The drawings include an exemplary embodiment where the garment is a compression sleeve that is wearable on the user's arm or leg. However, this is not a limitation on the present invention. FIGS. 1-7 show the garment or garment assembly 10 in accordance with a preferred embodiment of the present invention.

Figure 2:
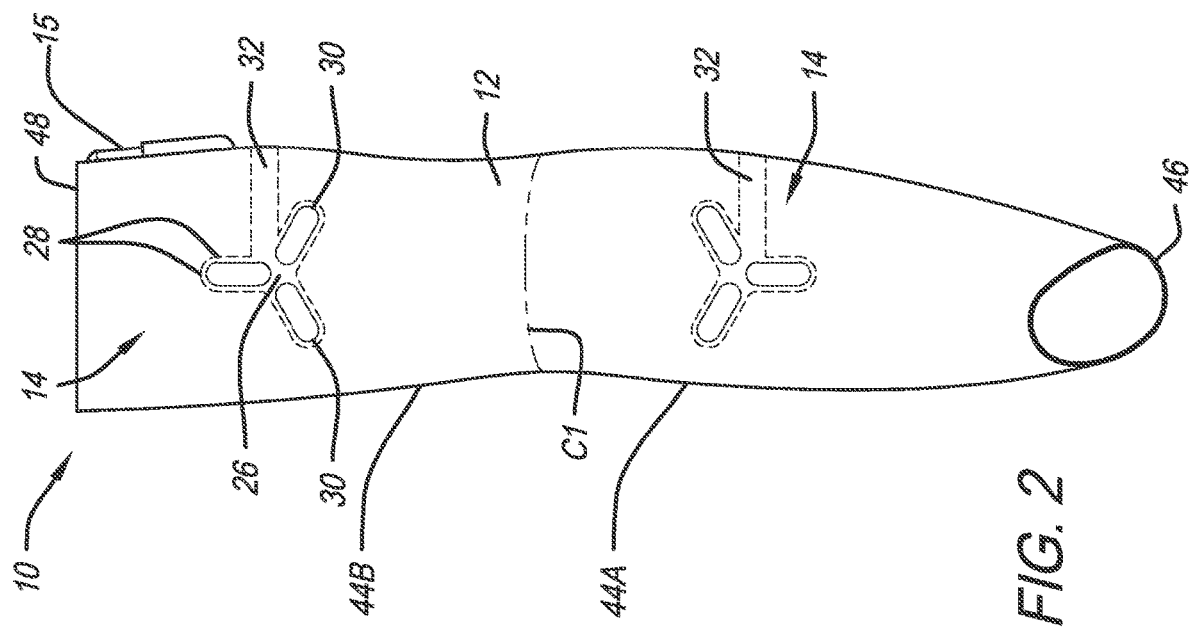
FIG. 2 is a front elevational view of the vibrating garment assembly of FIG. 1.
Figure 4:
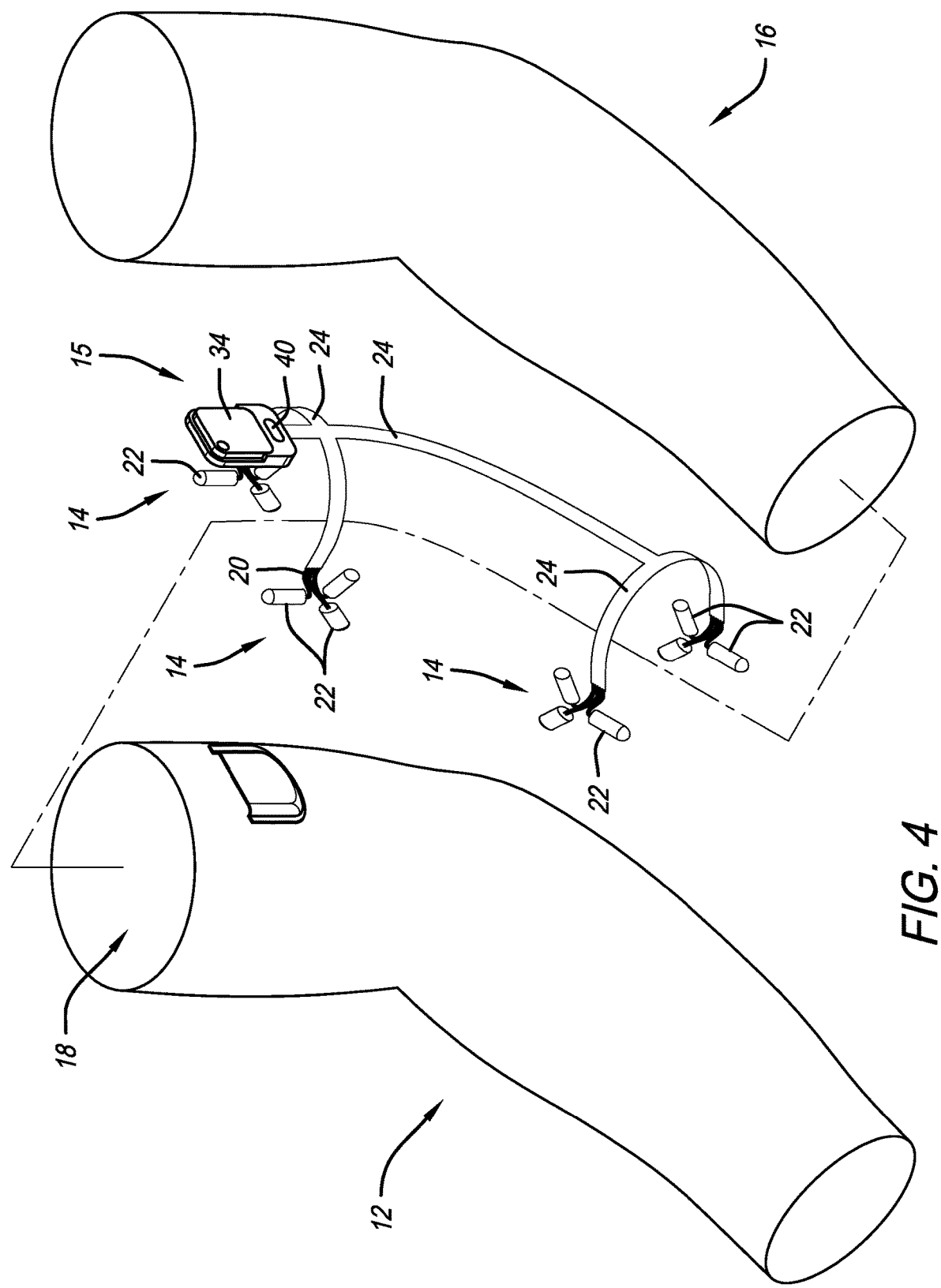
FIG. 4 is an exploded perspective view of the vibrating garment assembly of FIG. 1.

As shown in FIGS. 1-3, in a preferred embodiment, the garment assembly 10 generally includes an outer or first sleeve member 12, one or more vibration assemblies 14 and a control module 15. As shown in FIG. 4, in a preferred embodiment, the garment assembly 10 includes an inner or second sleeve member 16 that is positioned or disposed in the sleeve interior 18 of the first sleeve member 12. The vibration assemblies 14 and the other associated components, such as the wires 20 are sandwiched between the first sleeve member 12 and the second sleeve member 16. In another embodiment, instead of a full inner sleeve, patches or panels can be utilized to sandwich the vibration assemblies therebetween.

The vibration assemblies 14 preferably include a plurality of vibration motors 22 in a cluster or arrangement. Any number of vibration motors 22 (e.g., 1-10) can be included in a vibration assembly. Furthermore, the vibration devices can be any type of vibration motor or device. For example, the vibration devices can be puck shaped, similar to the vibration device used in a cell phone. In the embodiment shown in the drawings, the vibration motors 22 are cylindrical in shape. In a preferred embodiment, the vibration assembly 14 includes three or first, second and third vibration devices 22a, 22b and 22c that are arranged in a pattern as shown best in FIG. 5. As shown, the first, second and third vibration devices 22a, 22b and 22c are arranged in a circular pattern about a center point P1 and are each positioned an angle A1 from one another. Preferably, the angular distance or separation between each vibration device in the set or assembly is approximately the same. In a preferred embodiment, where three vibration devices are used, the second vibration device 22b is approximately 120° from the first vibration device 22a, the third vibration device 22c is approximately 120° from the first vibration device 22a, and the third vibration device 22c is approximately 120° from the second vibration device 22b. As used herein, the term "approximately" provides a range of within plus or minus 5°. In a preferred embodiment angle A1 (the angular distance) is the same or approximately the same between all vibration devices.

Figure 5:
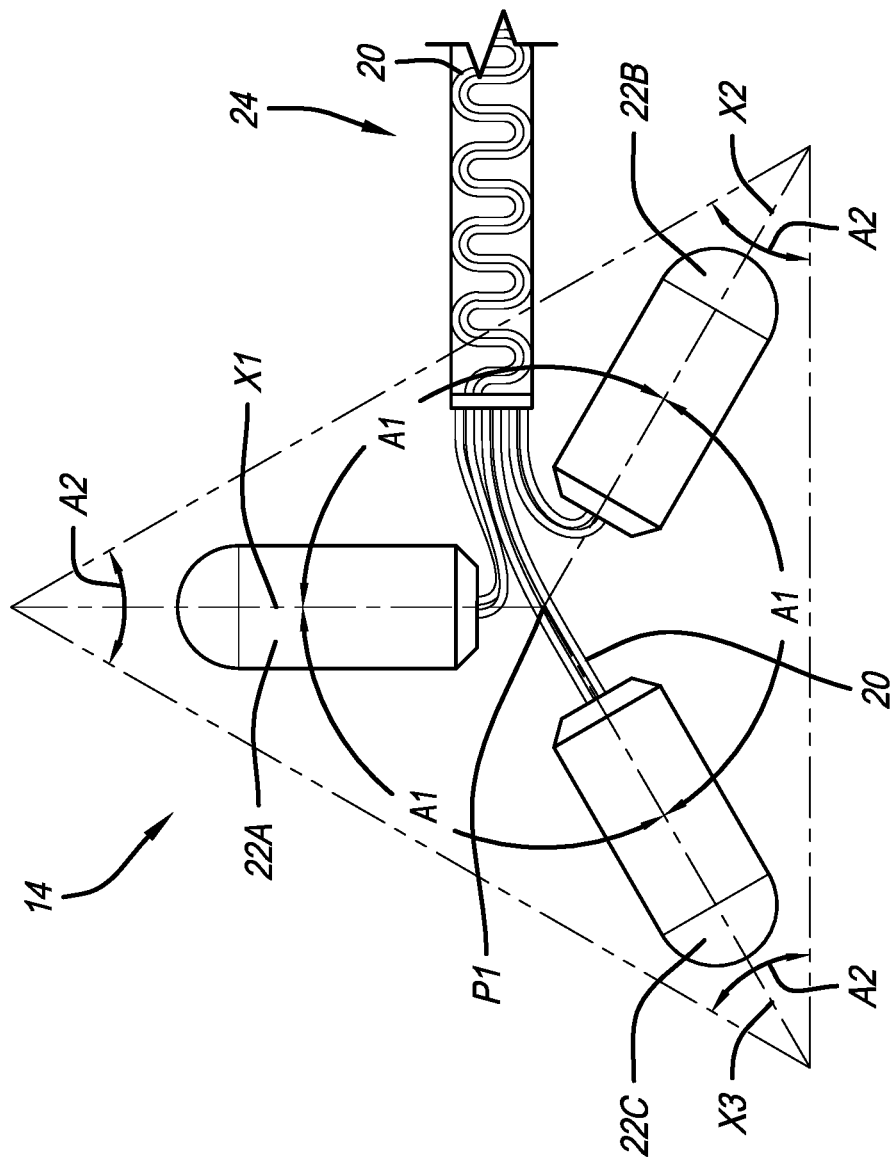
FIG. 5 is an elevational view of the vibration assembly of FIG. 1.

As is shown in FIG. 5, in a preferred embodiment, the first, second and third vibration devices 22a, 22b and 22c define first, second and third axes X1, X2 and X3. The first, second and third axes are co-planar (and extend generally parallel with the outer and inner surfaces of the garment assembly and the wearer's skin). It will be appreciated that when the garment assembly is worn, due to the undulations in the human body, the axes will not be co-planar. However, when the portion of the garment assembly that includes the vibration assembly is placed on a flat surface, the first, second and third vibration devices will be arranged as shown in FIG. 5. In this position, the axes are co-planar and this is the arrangement for purposes of the claims. As shown in FIG. 5, in this arrangement, the second axis X2 is approximately 120° from the first axis X1, the third axis X3 is approximately 120° from the first axis X1, and the third axis X3 is approximately 120° from the second axis X2 and the axes all pass through the center point P1.

FIG. 5 also includes a triangle T1 shown therein. This provides another way to quantify the arrangement of the vibration motors 22. Triangle T1 is an equilateral triangle (with angles A2 of 60°) with the first, second and third axes X1, X2 and X3 extending to and/or through the corners of the triangle. It will be appreciated that different shaped vibration devices can be used. For example, if puck or disk shaped vibration devices are used, the first, second and third axes may extend perpendicular to the outer and inner surfaces of the garment assembly and the wearer's skin. In such an arrangement, angle A1 may be measured from the center of the circular vibration device.

In a preferred embodiment, the wires 20 are part of a flexible or stretchable electronics (or electrical communication) layer, strip or the like (referred to herein as an electrical communication strip 24). The wires 20 are embedded or stitched into the electrical communication strip 24 in a pattern that provides slack in the wires 20 so that when the electrical communication strip 24 stretches during use, the wires 20 can move and do not tighten. See the pattern of the wires shown in FIG. 5.

In a preferred embodiment, the first sleeve member 12 is secured to the second sleeve member 16 at various locations using stitching 28. In a preferred embodiment, each vibration assembly 14 is housed or contained in a vibration assembly pocket 26. Preferably, the vibration assembly pocket 26 is defined or created by stitches 28 that extend closely around the outside of the vibration motors 22 and connect the first sleeve member 12 to the second sleeve member 16. As shown in FIG. 2, each of the vibration assembly pocket 26 includes a plurality of pocket fingers 30, one for each vibration motor 22. Preferably, the electrical communication strips 24 are housed or located within tunnels 32 that are created by connecting and/or stitching 28 the first and second sleeve members to one another, as shown in FIGS. 1-3.

As discussed herein, the material of the first and second sleeves and other portions of the garment assembly 10 (e.g., the electrical communication strip 24) can be made of an elastic, stretchable or compression material so that the garment provides compression to the body part that it is worn on. In a preferred embodiment, the garment assembly includes a compression gradient or change at one or more points or places between the distal end 46 and the proximal end 48 and along the length of the sleeve (see FIG. 2). The compression gradient may be gradual between the distal end 46 and the proximal end 48 or the garment may include two or more sections that each have different compression values. FIG. 2 shows first and second sections 44a and 44b that each include a different compression value. See dividing line C1 in FIG. 2, which delineates the change in compression value between the first or distal section 44a and the second or proximal section 44b. For example, the first section 44a may have a compression value of approximately 20 mmHg and the second section 44b have a compression value of approximately 15 mmHg. The sleeve may include more than two sections (e.g., 2-10 distinct sections). Or, the sleeve can be knitted or otherwise manufactured so that the compression changes gradually along at least a portion of the length of the sleeve such that the sleeve as a first compression value at the distal end and a second compression value at the second end, but the compression values gradually change over the length of the sleeve from the first compression value to the second compression value.

Figure 6:
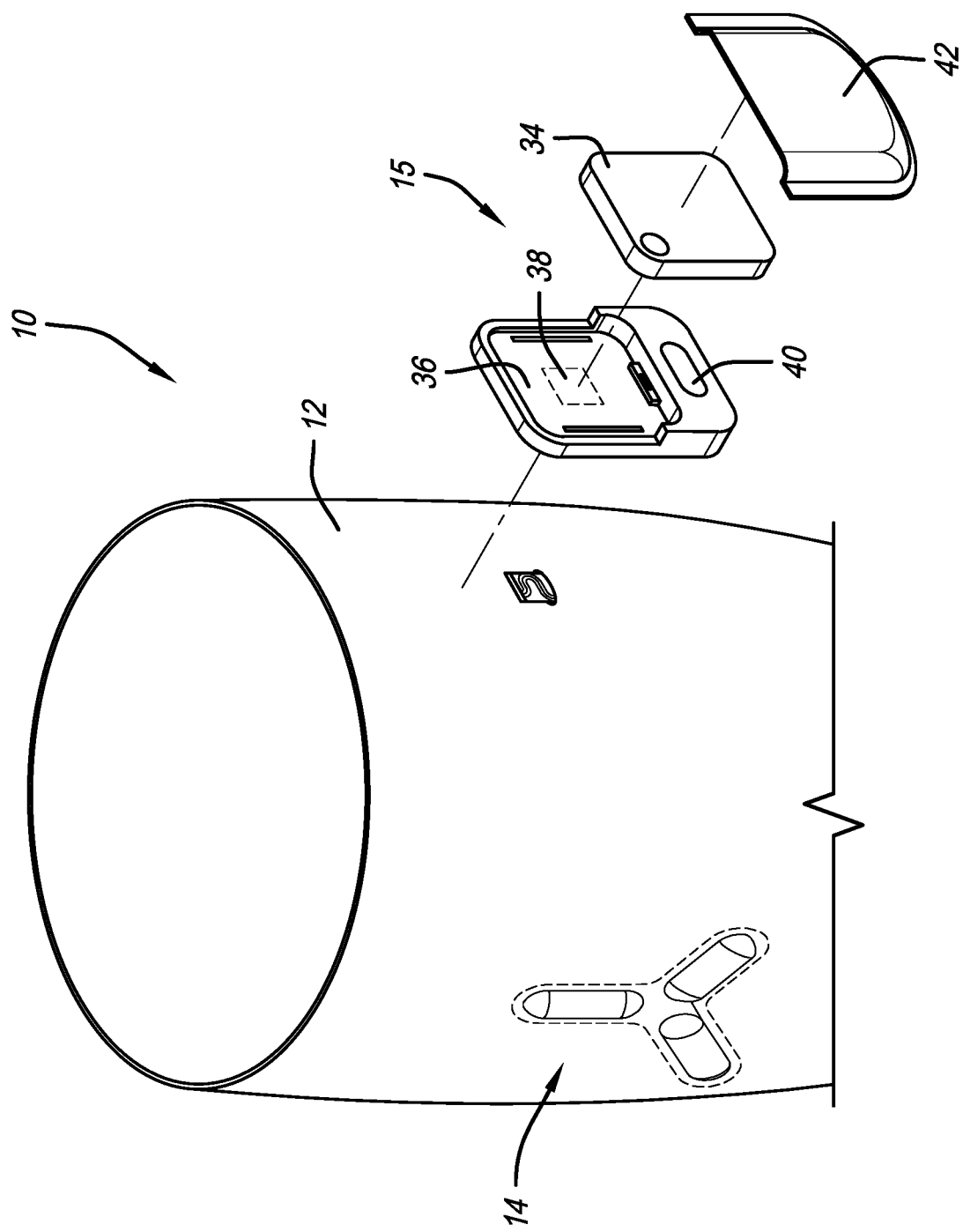
FIG. 6 is an exploded perspective view of a portion of the vibrating garment assembly and showing the control module.
Figure 7:
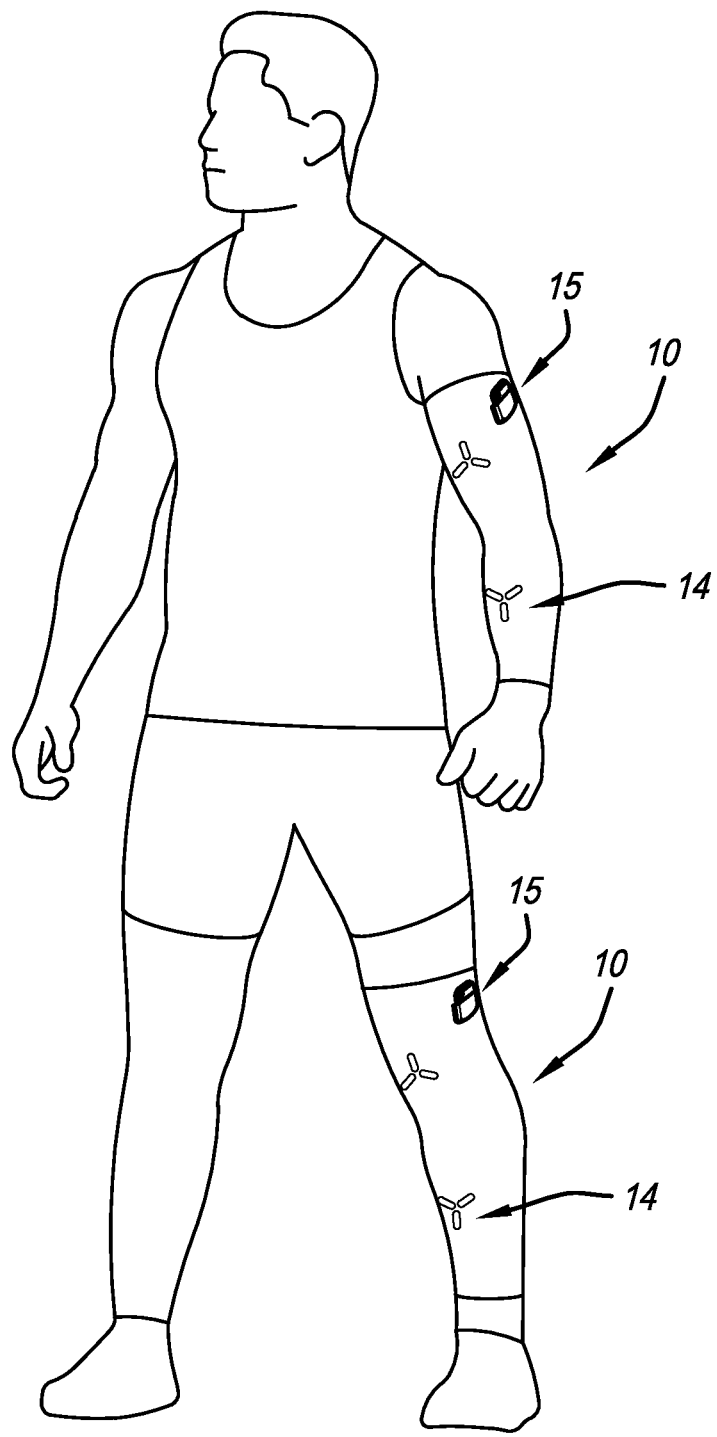
FIG. 7 is a depiction of a person wearing vibrating garment assemblies on their arm and leg.

As shown in FIG. 6, in a preferred embodiment, the control module 15 preferably includes a battery 34 that is received in a docking station 36. The docking station 36 may include a magnet 38 that is magnetically attracted to a magnet in the battery to help dock the battery in the docking station 36. The control module 15 can also include a switch or button 40 for turning the device on and off and/or cycling through different modes, frequencies and the like. In another embodiment, multiple switches or buttons can be used. The interior of the control module 15 preferably includes the memory, PCB, programming, wireless connection module and other electronics to control the device as desired and as described herein. As shown in FIG. 1, in a preferred embodiment, the control module 15 and the various components thereof are housed in a pocket 42 or other securing member. The pocket 42 can cover some or all of the control module 15. The entire control module can be removable or the docking station can be permanently attached (via stitching, welding or the like) to one or both of the inner and outer sleeves and the battery can be removable or replaceable. The control module and/or the battery can also have a port (e.g., USB-c) for charging, data connection, etc.

In a preferred embodiment, the vibration assemblies 14 are strategically located to target or provide therapy or vibration to certain body parts or muscles. For example, for the arm sleeve or garment assembly shown in FIGS. 1-7, four vibration assemblies 14 are included that are positioned over or adjacent to the bicep(s), tricep(s) and front and back of the forearm areas or muscles. In the leg sleeve or garment assembly shown in FIG. 7, the vibration assemblies 14 are positioned over or adjacent to the quadricep(s), hamstring(s), shin and calf areas or muscles. It will be appreciated that the term sleeve does not limit the garment assembly to be a single hollow sleeve for the arms or legs. A garment assembly that surrounds the torso, midsection, pelvic area, shoulders or any other body part (e.g., shirts, shorts, pants, straps, etc.) is/are also considered sleeves.

FIGS. 8-13 show another preferred embodiment, of a garment assembly 50 that generally includes a sleeve member 52. All description related to the embodiment shown and described in FIGS. 1-7 applies to all other embodiments described herein. In a preferred embodiment, sleeve member 52 is formed via a knitting process or method. With knitting, the thickness, compression level, stretchability and other properties can be varied throughout the sleeve member or garment. This method can be performed without the need for any or many seams and is similar to 3D printing. The knitting method allows the tunnels, vibration assembly pockets, control module pocket, etc. to be formed as part of the knitting process. The vibration motors 22 and electrical communication strips 24 (electrical wires and/or cables) are inserted into the tunnels and pockets as further described below and then preferably a single seam is used to close the sleeve member lengthwise (e.g., lengthwise with respect to the arm or leg) to create the sleeve interior through which a body part is placed.

Figure 8:
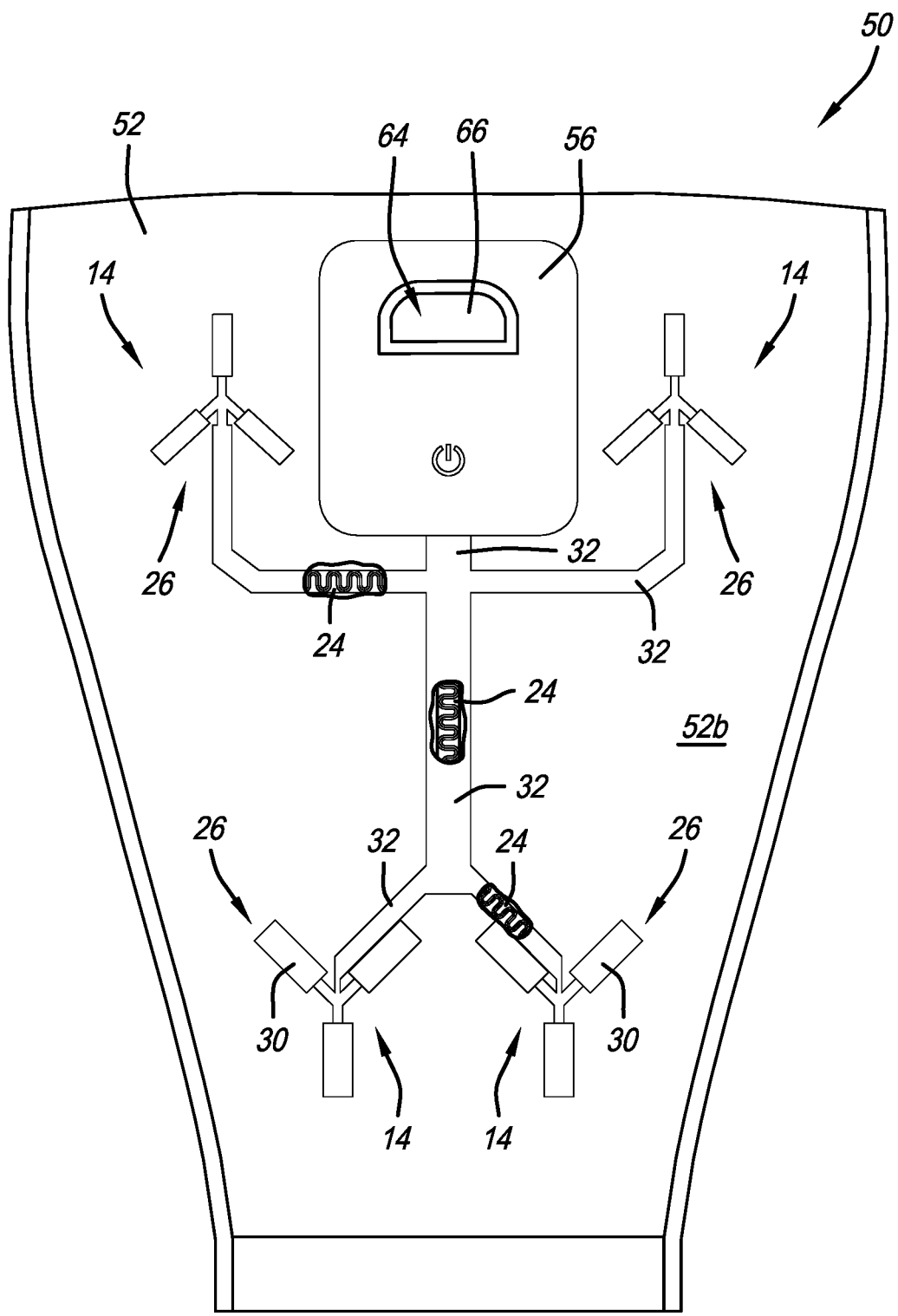
FIG. 8 is an elevational view of a vibrating garment assembly for the arm in accordance with a preferred embodiment of the present invention and prior to being formed into a sleeve.
Figure 9:
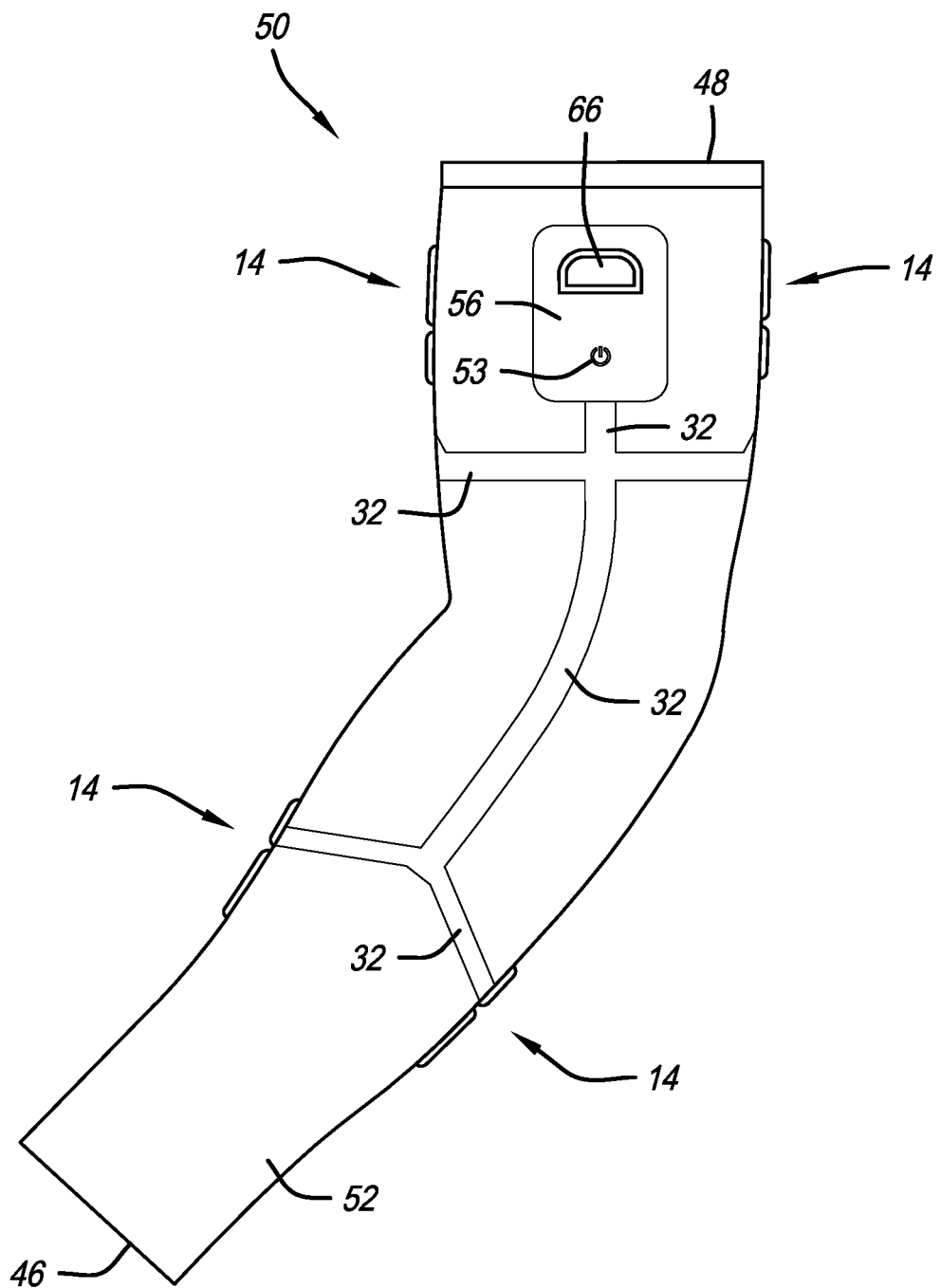
FIG. 9 is a side elevational view of the vibrating garment assembly of FIG. 8.
Figure 10:
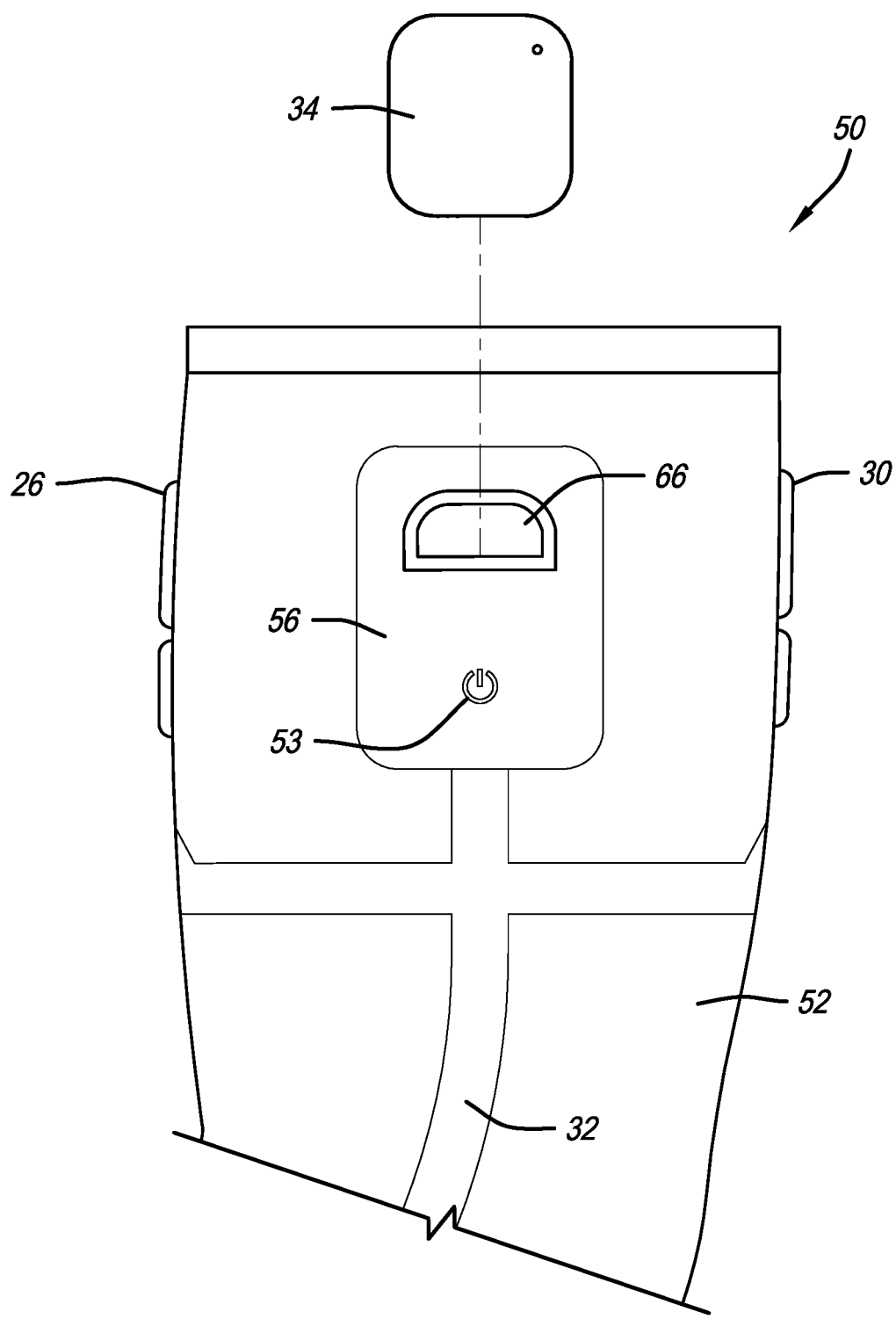
FIG. 10 is an elevational view of a portion of the vibrating garment assembly of FIG. 8 with the battery exploded out of the pocket.

It should be appreciated that FIG. 8 shows the garment assembly 50 prior to being formed into a cylindrical sleeve. In a preferred embodiment, the garment assembly 50 generally includes sleeve member 52 that includes an inner surface 52a and an outer surface 52b, one or more vibration assemblies 14 and a control module 54. The vibration assemblies 14 are similar to those described above and, therefore, an explanation will be omitted here. In a preferred embodiment, the wires 20 are part of a flexible or stretchable electronics (or electrical communication) layer, strip or the like (referred to herein as an electrical communication strip 24). The wires 20 are embedded or stitched into the electrical communication strip 24 in a pattern that provides slack in the wires 20 so that when the electrical communication strip 24 stretches during use, the wires 20 can move and do not tighten. See the pattern of the wires shown in FIGS. 5 and 8.

In a preferred embodiment, each vibration assembly 14 is housed or contained in a vibration assembly pocket 26. Preferably, the vibration assembly pocket 26 is defined or created via the knitting process and the vibration assembly pocket outer edges extend closely around the outside of the vibration motors 22. As shown in FIG. 8, each of the vibration assembly pockets 26 includes a plurality of pocket fingers 30, one for each vibration motor 22. Preferably, the electrical communication strips 24 are housed or located within tunnels 32 that are also created via the knitting process. Preferably, the sleeve member 52 also includes indicia 53 or a marking, such as the power symbol thereon that overlies the button 40 in the control module. This shows the user wear to push on the sleeve member to depress the button 40 therebehind.

Figure 11:
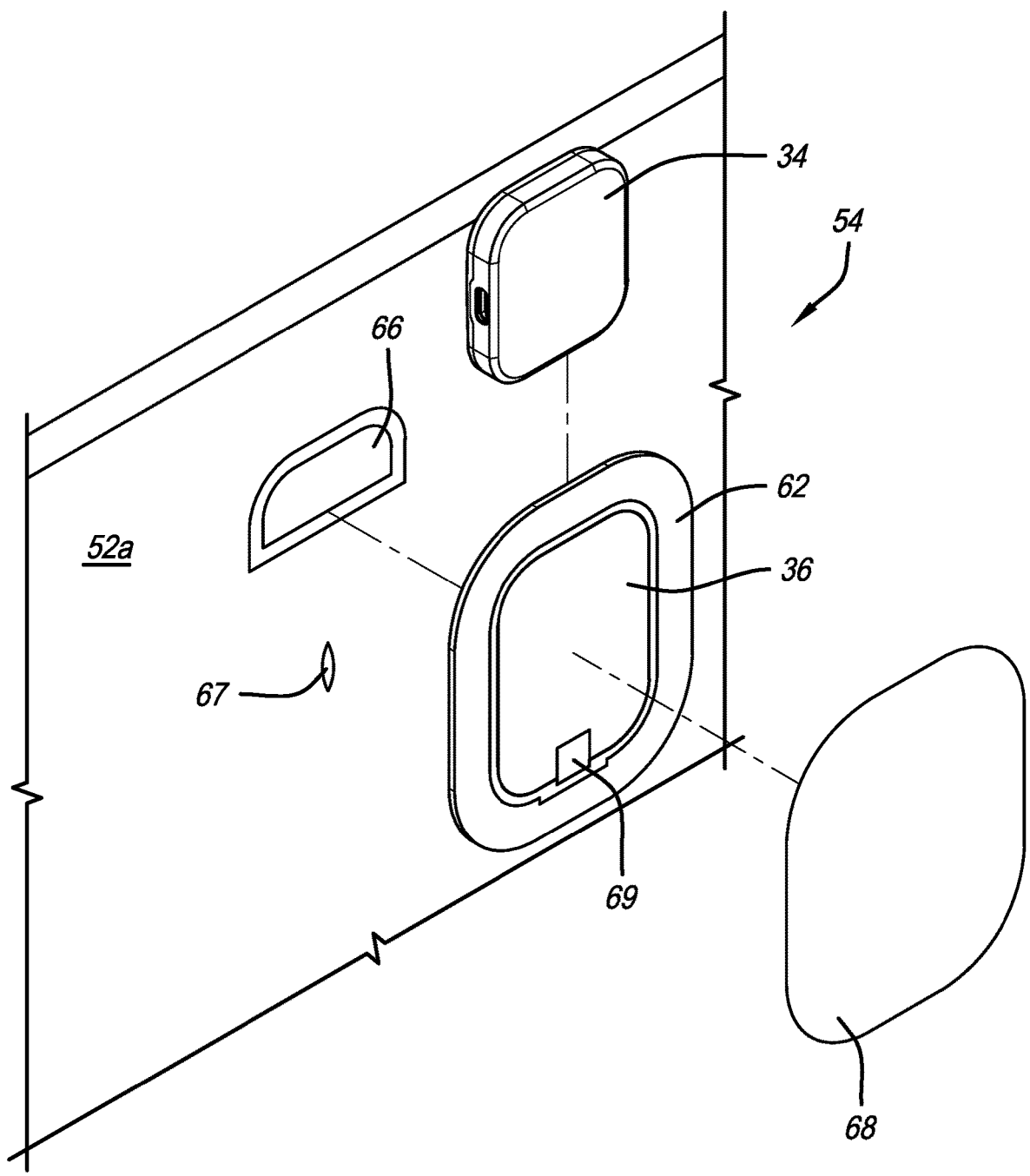
FIG. 11 is an exploded perspective view of the inner side of the sleeve member with the docking station and patch exploded therefrom.
Figure 12:
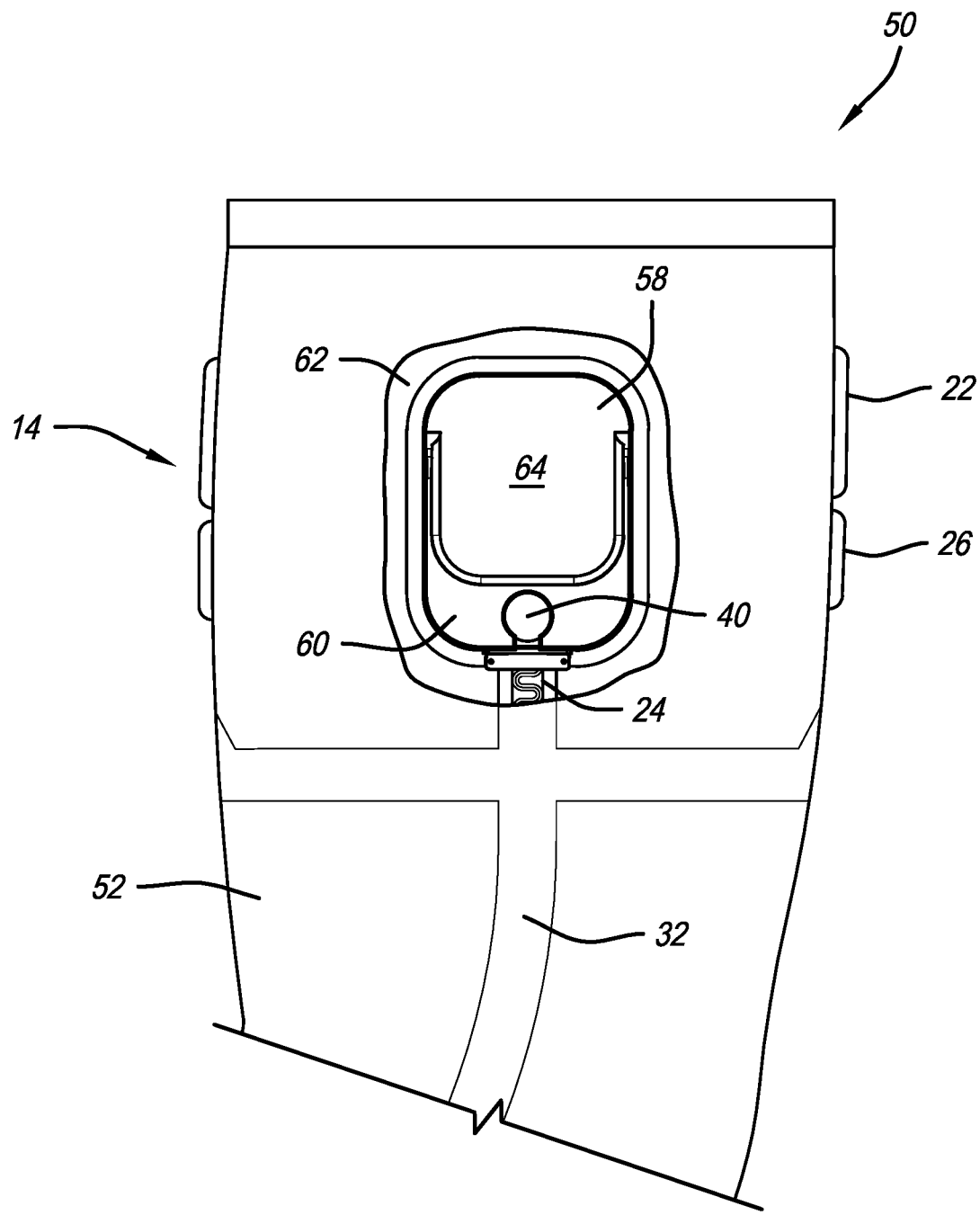
FIG. 12 is an elevational view of a portion of the vibrating garment assembly of FIG. 8 with a portion of the pocket cut away to show the docking station.
Figure 13:
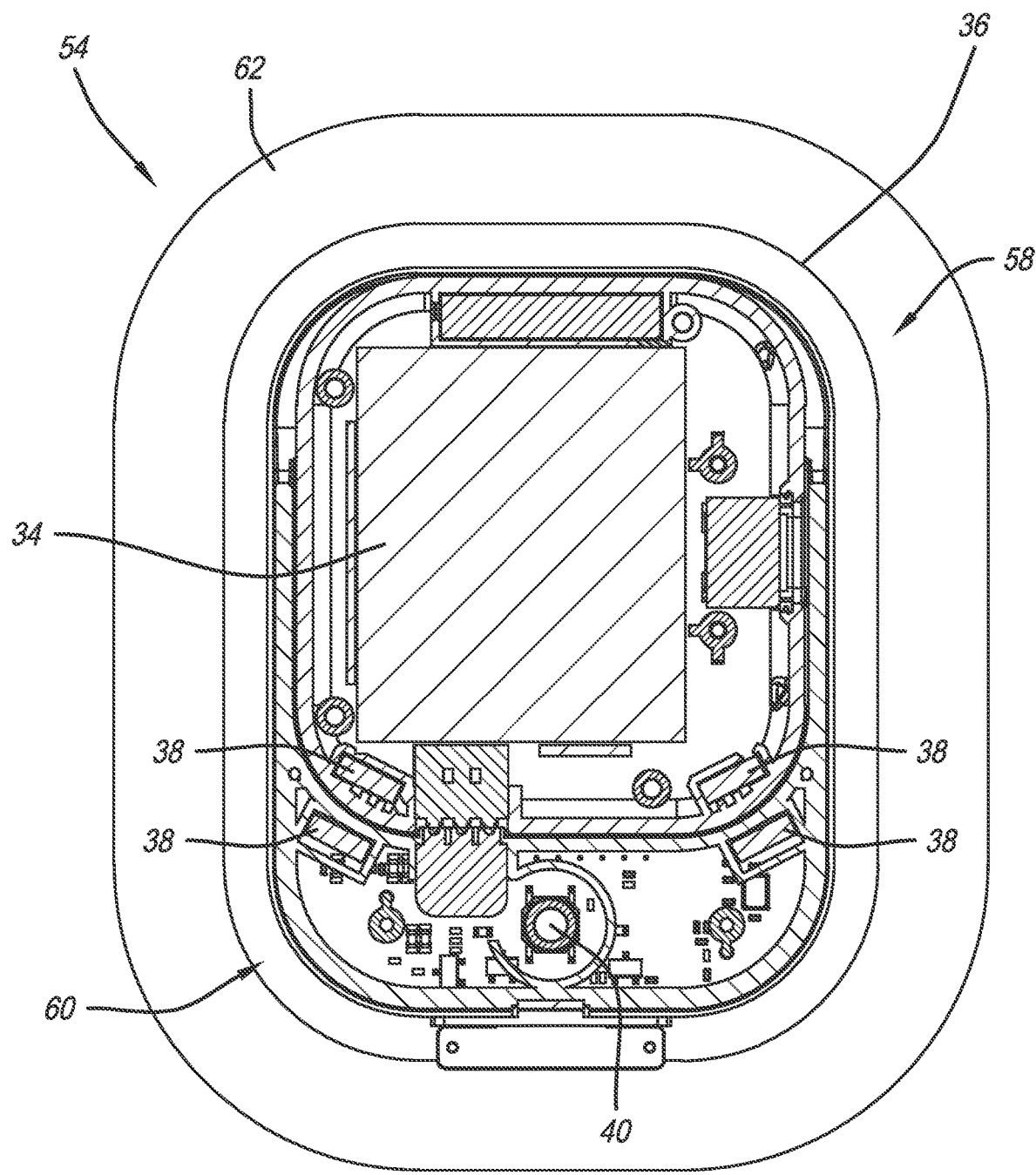
FIG. 13 is an elevational view of the control module with a portion of the battery and docking station removed to see the internal components.

As shown in FIGS. 11-13, in a preferred embodiment, the control module 54 preferably includes battery 34 that is received in docking station 36. The docking station 36 may include one or more magnets 38 that are magnetically attracted to one or more magnets in the battery 34 to help dock the battery in the docking station 36 (see FIG. 13). The control module 54 can also include a switch or button 40 for turning the device on and off and/or cycling through different modes, frequencies and the like. In another embodiment, multiple switches or buttons can be used. The interior of the control module 15 preferably includes the memory, PCB, programming, wireless connection module and other electronics to control the device as desired and as described herein.

FIGS. 11-12 shows a preferred process for securing the docking station 36 to the sleeve member 52 and for defining a control module pocket 56. In a preferred embodiment, the docking station 36 includes a battery portion 58 (that receives the battery 34) and a control portion 60 (that houses at least a portion of the electrical components, e.g., button 40, PCB, etc.). The docking station 36 also includes an outer flange 62 extending therearound. The outer flange 62 is secured to the inner surface 52a of the sleeve member 52. Because the battery portion 58 is recessed within the docking station 36, when the docking station 36 is secured to the inner surface 52a of the sleeve member, a battery space 64 is defined between battery portion 58 and the inner surface 52a. The sleeve member 52 includes a battery opening 66 defined therethrough that communicates the battery space 64 with the outside or exterior of the sleeve member 52. This allows the battery 34 to be removed from an inserted into the docking station 36/control module 54 (see FIG. 10). In a preferred embodiment, an inner layer member 68 is secured to the inner surface 36a of the docking station and the inner surface 52a of the sleeve member 52 to partially form the control module pocket and to help secure the control module 54 in place.

FIG. 11 also shows a slit 67 through which the vibration assemblies 14 and electrical communication strips 24 can be inserted into the tunnel(s) 32 and fed or moved to the appropriate positions during manufacture. The sleeve member 52 preferably provides a number of slits for this purpose. As is also shown in FIG. 11, in an embodiment of the invention, the garment assembly 50 can include one or more biometric sensors 69 or the like. As described herein, the biometric sensor(s) or a biometric detection, sensor or tracking system can be used to monitor, determine and analyze different biometric data or indices of the user. For example, the garment assembly 50 can include the ability to monitor, heart rate/pulse, heart rate variability, blood oxygen letter, skin, muscle or body part temperature. The data and information collected by the biometric tracking system can be communicated to the software application to provide the user with recommendations for use of the garment assembly 50. The biometric data can also be used to control the vibration assemblies 14 and turn them on and off at different times based on predetermined data points or levels detected by the software (e.g., in the control module 54 or the remote/mobile application). For example, once a predetermined score or level of strain (calculated or otherwise) has been reached or sensed, one or more of the vibration assemblies or individual vibration devices can be switched on (e.g., for a predetermined period of time, in cycles or as otherwise desired or determined by the software).

Figure 14:
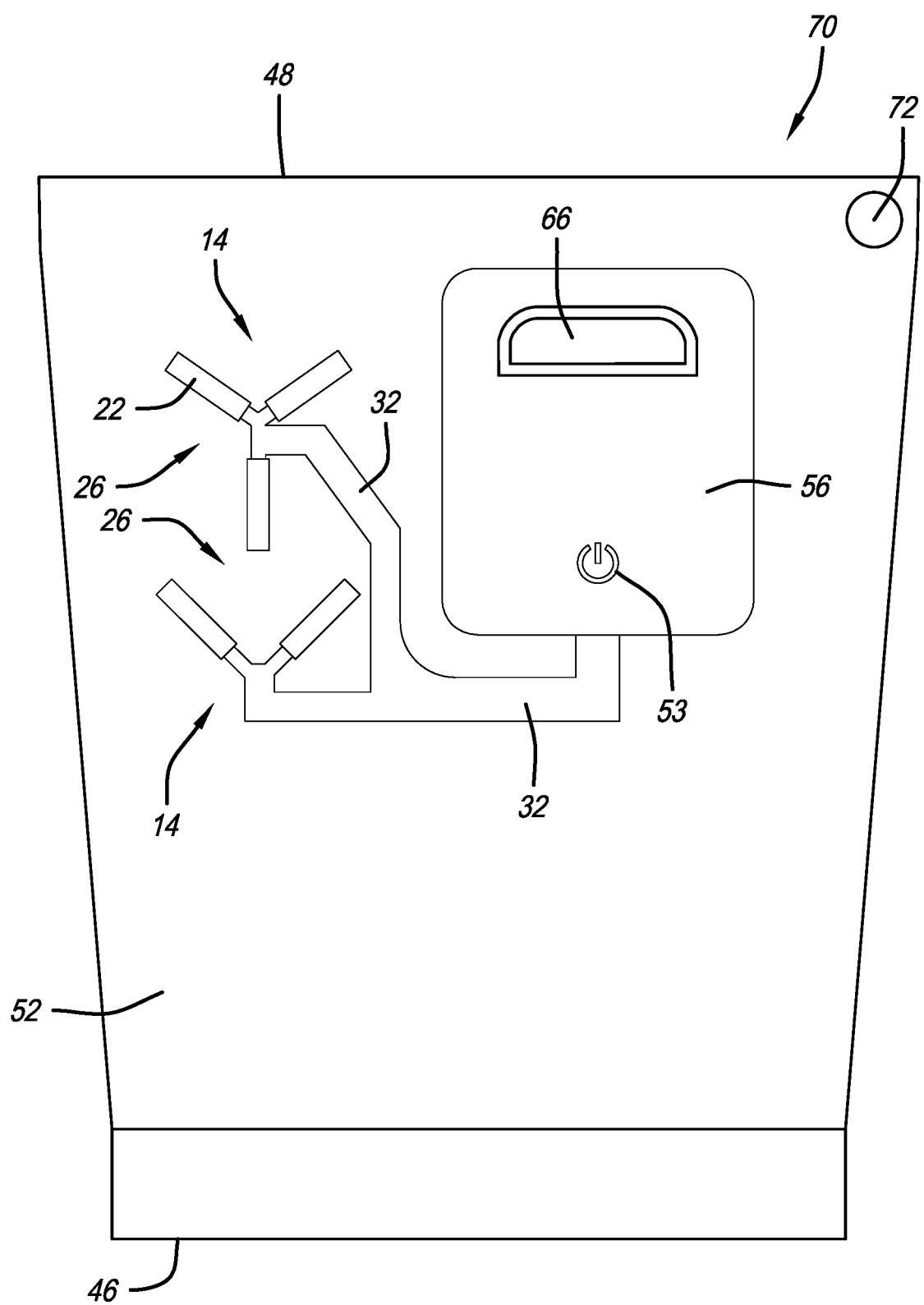
FIG. 14 is an elevational view of a vibrating garment assembly for the calf in accordance with a preferred embodiment of the present invention and prior to being formed into a sleeve.

FIG. 14 shows a garment assembly 70 for use on a wearer's calf. Garment assembly 70 is similar to the other garment assemblies described herein and all description related to other embodiments apply to garment assembly 70. It should be appreciated that FIG. 14 shows the garment assembly 70 prior to being formed into a cylindrical sleeve. Garment assembly 70 includes first and second vibration assemblies 14. The first vibration assembly includes three vibration motors 22 and the second vibration assembly includes two vibration motors 22. In a preferred embodiment, the sleeve member 52 includes a centering mark 72 thereon. When using the garment assembly 70 for the calf, the control module must be placed to the side of the shin bone. When putting the garment assembly 70 on, the user can align the centering mark 72 with their shin bone so that the control module will be positioned on the side of the calf and the first and second vibration assemblies 14 will overly the calf.

Figure 15:
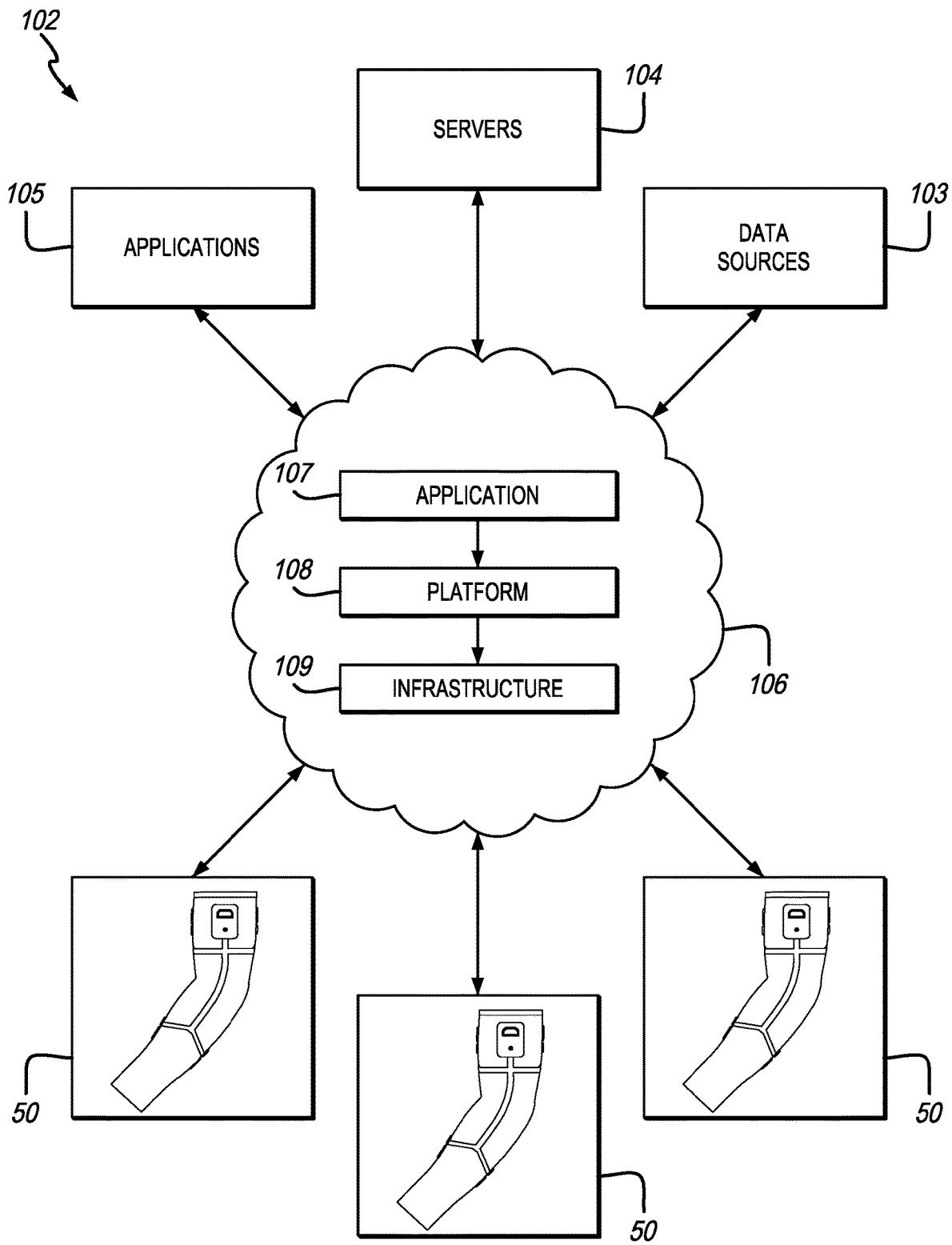
FIG. 15 is a system block diagram showing structure of a vibration therapy system.

FIG. 15 is a system block diagram showing structure of a garment assembly system 102. The garment assembly system 102 includes one or more garment assemblies 50, data sources 103, servers 104, applications 105, and a cloud 106.

The data sources 103 include, for example, online or cloud-based data sources of health and wellness information. The health and wellness information may be aggregated data from a number of unorganized sources upon which statistical analysis can be done. The data sources 103 may also include biometric information from wearable biometric devices, such as, for example, Biostrap wearable devices, Apple® wearable devices, and the like. The data sources 103 may include information from Apple's Apple Health application, MyFitnessPal application, and the like.

The servers 104 and applications 105 are well known to one of ordinary skill in the art. The servers 104 may include structure configured to facilitate processing and data storage and transfer. The applications 105 may be standalone applications configured to be executed on a smart device, a standalone computer, a laptop, an entertainment center, or other computing devices.

In this embodiment, the cloud 106 includes an application 107, a platform 108, and an infrastructure 109. For example, the application 107 may include a variety of applications configured to execute all or portions of the functions of an intelligence engine in connection with the platform 108 and the infrastructure 109. One of ordinary skill in the art would understand that the cloud 106 and its constituents therein is only one way to depict a cloud-based computing system and there are a variety of other ways to depict the same without departing from the scope of the present invention.

Figure 16:
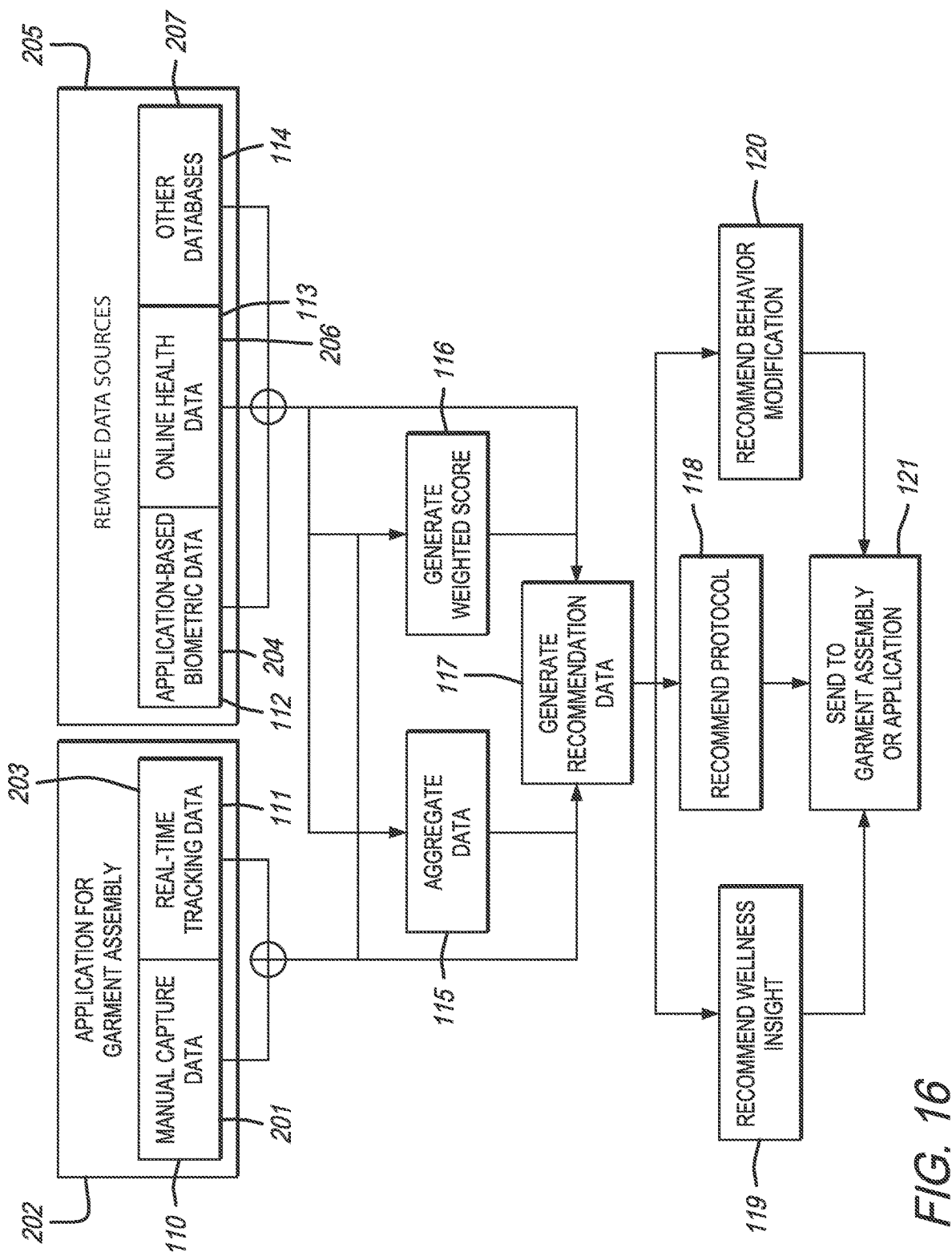
FIG. 16 is a flow diagram depicting a method of providing therapeutic effect using a garment assembly utilizing an intelligence engine in accordance with an embodiment of the present invention.

FIG. 16 is a flow diagram depicting a method of providing therapeutic effect using a garment assembly 10 or 50 (garment assembly 50 is shown in the drawings) utilizing the intelligence engine in accordance with an embodiment of the present invention.

At Step 110, manual capture data 201 is generated. The manual capture data 201 is, for example, data input via the touch screen of a mobile device or tablet. An application 202 running on a smart device associated with the touch screen may prompt a user to input answers to questions regarding health, wellness, or other parameters useful to provide recommendation data to the user. Alternatively, though not shown in connection with FIG. 16, a user may input data directly into the garment assembly 50, which may then be transferred wirelessly to be used by the intelligence engine.

At Step 111, real-time tracking data 203 is generated. In the embodiment depicted in FIG. 16, an application 202 configured to wirelessly connect to the garment assembly 50 monitors and stores real-time tracking data of a user's use of the garment assembly 50. In an embodiment, the application 202 transmits the real-time tracking data to a cloud-based computing system such as that shown in FIG. 15. In other embodiments, a standalone computing system may be utilized.

At Step 112, application-based biometric data 204 is provided via one of a remote data sources 205. At Step 113, online health data 206 is provided via another one of the remote data sources 205. At Step 114, data from other databases 207 is provided via another one of the remote data sources 205. One of ordinary skill in the art would understand that the remote data sources 205 may include the data sources 103.

One of ordinary skill in the art would understand that the various input data described herein may be substituted for the particular input data described in connection with FIG. 16 without departing from the scope or spirit of the present invention.

At Step 115, all or portions of the manual capture data 201, real-time tracking data 203, application-based biometric data 204, online health data 206, and data from the other databases 207 are aggregated. One of ordinary skill in the art would understand the methodology for data aggregation, and as more fully described herein. In an embodiment, third party data and user data are aggregated separately. In another embodiment, all data is aggregated.

At Step 116, a weighted score is generated based on all or portions of the manual capture data 201, real-time tracking data 203, application-based biometric data 204, online health data 206, and data from the other databases 207. The weighted score may include a recovery determination score, a wellness determination score, and a behavior determination score. As an example, the recovery determination score includes a determination of how long a user's HB returned to a restorative state. Depending on the application's parameters, the score could, for example, determine that a Recovery Score is Poor, as described more fully below in Table 1. As another example, a wellness determination score includes a determination of dietary intake and trends to determine an overall wellness score. Depending on the application's parameters, the score could, for example, determine that a data input regarding dietary intake was within predetermined parameters, thereby increasing the user's wellness determination score. As another example, a behavior determination score includes a determination of sleep metrics and trends to determine an overall behavior determination score. Depending on the application's parameters, the score could, for example, determine that a Sleep Metrics score was Poor, as described more fully below in Table 1.

At Step 117, recommendation data is generated based on all or portions of (1) the aggregated data (2) the weighted score and (3) all or portions of the manual capture data 201, real-time tracking data 203, application-based biometric data 204, online health data 206, and data from the other databases 207. These data may all be combined to generate the recommendation data. Alternatively, only a weighted score is utilized to generate the recommendation data. In yet another alternative, only real-time tracking data 201 is utilized to generate the recommendation data. One of ordinary skill in the art would understand the various data inputs are fluid and may be utilized based on desired parameters for optimum health and wellness.

At Step 118, a recommended protocol is determined as part of the recommendation data. The recommended protocol is, in an embodiment, obtained from a library of protocols. For example, see FIGS. 26-29 in the '955 publication, which show various protocols that may be obtained from the library of protocols for a percussive massage device. Similar protocols, including time, speed, motor or motor set, pattern (e.g., continuously on, wave, pulse, etc.) and other features can be included in the protocols or routines for the garment assembly. In another embodiment, the recommended protocol is synthesized from available data, i.e., a "bespoke" routine synthesis suitable for a particular user. Table 1 below depicts how routines of the protocol may be prioritized and/or steps within each of the routines may be modified to accommodate various data inputs. For example, the recommended protocol may consist of more than one routine.

At Step 119, a wellness insight is recommended as part of the recommendation data. The wellness insight, for example, may be based on the weighted score that determines that the user's dietary intake is poor and thus, would provide an insight that may assist the user to modify their dietary intake. Other examples are within the scope of the present invention.

At Step 120, a behavior modification is recommended as part of the recommendation data. The behavior modification, for example, may be based on the weighted score that determines that a user's Sleep Metrics are Poor, thereby prompting a behavior modification notification to the user to alert the user about his or her poor sleep habits.

At Step 121, one or more of the recommended protocol, wellness insight, or behavior modification is provided to the device 400 or the application 202. Preferably, the user of the device 400 is notified in accordance with the recommendation data.

Table 1 below provides an example of input data and output data for a particular scenario in accordance with a preferred embodiment.

| INTELLIGENCE ENGINE | |
| --- | --- |
| INPUT DATA | OUTPUT DATA |
| Female | Modification of steps in routines |
| 57 | Modification of steps in routines |
| Activity = Run | Prioritization of specific routines and personalized notifications |
| Duration = 51 minutes | Prioritization of specific routines and the modification of steps within them |
| Distance = 8 miles | Prioritization of specific routines and the modification of steps within them |
| Trends = X % Faster and longer than normal | Prioritization of specific routines and the modification of steps within them |
| Time = Evening | Prioritization of second series of routines and personalized notifications |
| Time = Within 2 hours of activity completion | Prioritization of specific routines, and personalized notifications |
| Recent Vibration Therapy = Short + Infrequent | Modification of steps in routines and highlighting of insights |
| Recovery Score = Poor | Prioritization of specific routines, the modification of steps within them, personalized notifications, and highlighting of insights |
| Sleep Metrics = Poor | Prioritization of specific routines, the modification of steps within them, personalized notifications, and highlighting of insights |

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present invention. Other measurements or dimensions are within the scope of the invention.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A washable garment assembly, comprising:
    a sleeve member, comprising:
        an inner surface;
        an outer surface; and
        a tunnel defined between the inner surface and the outer surface;
    a first vibration assembly associated with the sleeve member and permanently sealed between the inner surface and the outer surface, wherein the first vibration assembly includes at least a first vibration motor, wherein the first vibration motor is waterproof enclosed; and
    a control module associated with the sleeve member and in electrical communication with the first vibration assembly, wherein the control module comprises:
        a battery; and
        a docking station that includes a battery portion and a control portion,
    wherein the docking station is secured to the inner surface of the sleeve member,
    wherein a battery space is defined between the battery portion and the inner surface of the sleeve member,
    wherein the sleeve member includes a battery opening defined therethrough that couples the battery space with an exterior of the sleeve member,
    wherein the battery is removable from the control module through the battery opening, and
    wherein the tunnel fully extends between the first vibration assembly and the control module,
    wherein the washable garment assembly is washable after removing the battery through the battery opening.

2. The washable garment assembly of claim 1, wherein the sleeve member comprises a knitted material, wherein the sleeve member includes a first vibration assembly pocket defined within the sleeve member and between the inner and outer surfaces, and
    wherein the first vibration motor is disposed in the first vibration assembly pocket.

3. The washable garment assembly of claim 2, further comprising an electrical communication strip that includes a stretchable fabric member and at least a wire that is secured to the stretchable fabric member,
    wherein the wire extends between the control module and the first vibration motor,
    wherein the wire is formed in a slack pattern when the stretchable fabric member is in a normal position, and
    wherein the stretchable fabric member is configured to stretch in a longitudinal direction and the wire is configured to straighten when the stretchable fabric member is stretched in the longitudinal direction.

4. The washable garment assembly of claim 3, further comprising a control module pocket that contains the control module, wherein the tunnel fully extends between the first vibration assembly pocket and the control module pocket, and wherein the tunnel contains the electrical communication strip.

5. The washable garment assembly of claim 4, wherein the first vibration assembly includes a second vibration motor, wherein the first vibration assembly pocket includes first and second pocket fingers, and wherein the first vibration motor is positioned in the first pocket finger and the second vibration motor is positioned in the second pocket finger.

6. The washable garment assembly of claim 1, wherein the docking station further includes an outer flange extending therearound, and wherein the outer flange is secured to the inner surface of the sleeve member.

7. The washable garment assembly of claim 6, wherein an inner layer member is secured to an inner surface of the docking station and the inner surface of the sleeve member to form the control module pocket that houses the control module.

8. The washable garment assembly of claim 1, further comprising a second vibration assembly associated with the sleeve member,
    wherein the second vibration assembly includes a plurality of vibration motors that are arranged in a circle about a center point,
    wherein an angular distance between each vibration motor of the plurality of vibration motors is approximately the same, and
    wherein the first vibration assembly is positioned to target a first body part and the second vibration assembly is positioned to target a second body part when the garment assembly is worn by a user.

9. The washable garment assembly of claim 1, wherein the sleeve member includes a distal end and a proximal end, and a sleeve length is defined between the proximal end and the distal end, and wherein the sleeve member includes a first section with a first compression value and a second section with a second compression value.

10. The washable garment assembly of claim 9, wherein the second section is defined between the first section and the proximal end, and wherein the first compression value is greater than the second compression value.

11. The washable garment assembly of claim 1, wherein the sleeve member defines a sleeve length between a distal end and a proximal end, wherein the sleeve member comprises a material that includes a range of compression values that decrease from the distal end to the proximal end.

12. The washable garment assembly of claim 1, wherein the sleeve member comprises a germanium alloy that is configured to emit infrared radiation.

13. The washable garment assembly of claim 1, wherein the sleeve member comprises a biometric sensor.

14. The washable garment assembly of claim 1, wherein the docking station includes a first magnet and the battery includes a second magnet, and wherein the first magnet is magnetically attracted to the second magnet when the battery is received in the docking station.

15. The washable garment assembly of claim 1, wherein at least one of the control module, the battery, and the docking station are removable from the garment assembly prior to washing.

16. The washable garment assembly of claim 1, wherein the sleeve member is a sock, and wherein the first vibration assembly and the control module are arranged in a layer of the sock.

17. A method of forming a washable garment assembly, the method comprising the steps of:
   forming a garment member using a knitting process, wherein the garment member includes an inner surface and an outer surface, wherein during the knitting process at least a tunnel and at least a vibration assembly pocket are formed within the garment member and between the inner and outer surfaces, and wherein a slit is formed in the inner surface of the garment member;
   coupling a control module to the garment member, wherein the tunnel fully extends between the vibration assembly pocket and the control module, wherein the control module comprises a docking station and a battery;
   obtaining a vibration assembly that includes at least a vibration motor, wherein the vibration motor is waterproof enclosed, wherein the vibration motor includes at least a wire connected thereto;
   inserting the vibration motor and the wire through the slit;
   maneuvering the vibration motor into the vibration assembly pocket;
   maneuvering the wire into the tunnel; and
   sealing the vibration motor between the inner surface and the outer surface, such that the vibration motor is permanently embedded within the washable garment assembly,
   wherein the washable garment assembly is washable after removing the battery from the control module.

18. The method of claim 17, further comprising:
   forming a battery opening through the garment member, wherein the docking station comprises a battery portion and a control portion,
   wherein coupling the control module to the garment member comprises securing the docking station to the inner surface of the garment member,
   wherein a battery space is defined between the battery portion and the inner surface of the garment member,
   wherein the battery opening couples the battery space with an exterior of the garment member, and
   wherein the battery is removable through the battery opening.

19. The method of claim 18, wherein the docking station comprises an outer flange extending therearound, and wherein the securing the docking station to the inner surface of the garment member comprises securing the outer flange to the inner surface of the garment member.

20. The method of claim 19, further comprising:
   obtaining an inner layer member; and
   securing the inner layer member to an inner surface of the docking station and the inner surface of the garment member to form a control module pocket that houses the control module,
   wherein the tunnel extends between the control module pocket and the vibration assembly pocket, and wherein the wire electronically couples the control module and the vibration motor.

21. The method of claim 17, further comprising closing the garment member using a single seam to create a sleeve interior through which an arm or a leg is placed.

* * * * *